US009708568B2

(12) United States Patent
Holland et al.

(10) Patent No.: US 9,708,568 B2
(45) Date of Patent: *Jul. 18, 2017

(54) FRAGRANCE COMPOSITIONS

(71) Applicant: The Procter & Gamble Company, Cincinnati, OH (US)

(72) Inventors: Lynette Anne Makins Holland, Abbots Langley (GB); Julien Claude Plos, London (GB); Sandra Sabine Meyer, Twickenham (GB); Lara Katharine Goodman, Woking (GB); Christelle Marie Sandrine Bonnet, Caillouet-Orgeville (FR); Fabienne Pastor, Meriel (FR); Jose Maria Velazquez, Ascot (GB); Jonathan Richard Stonehouse, Windlesham (GB); William Eoghan Staite, Egham (GB); Jonathan Robert Cetti, Mason, OH (US); Zerlina Guzdar Dubois, Mason, OH (US); Virginia Tzung-Hwei Hutchins, Cincinnati, OH (US); Michael Wayne Kinsey, Lebanon, OH (US); Christine Marie Readnour, Fort Mitchell, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/705,373

(22) Filed: May 6, 2015

(65) Prior Publication Data

US 2015/0322376 A1   Nov. 12, 2015

Related U.S. Application Data

(60) Provisional application No. 61/988,912, filed on May 6, 2014.

(51) Int. Cl.
*A61K 8/18* (2006.01)
*A61Q 13/00* (2006.01)
*C11B 9/00* (2006.01)
*A61K 8/49* (2006.01)
*A61Q 19/00* (2006.01)

(52) U.S. Cl.
CPC .......... *C11B 9/0011* (2013.01); *A61K 8/4926* (2013.01); *A61Q 13/00* (2013.01); *A61Q 19/00* (2013.01); *C11B 9/00* (2013.01); *C11B 9/008* (2013.01); *C11B 9/0015* (2013.01); *C11B 9/0019* (2013.01); *C11B 9/0023* (2013.01); *C11B 9/0034* (2013.01); *C11B 9/0061* (2013.01); *C11B 9/0069* (2013.01); *C11B 9/0092* (2013.01); *C11B 9/0096* (2013.01)

(58) Field of Classification Search
CPC ... C11B 9/0011; C11B 9/0015; C11B 9/0023; C11B 9/0034; C11B 9/0061; C11B 9/0069; C11B 9/0092
USPC .............................................................. 512/6
See application file for complete search history.

(56) References Cited

U.S. PATENT DOCUMENTS

| | | |
|---|---|---|
| 4,430,243 A | 2/1984 | Bragg |
| 5,538,719 A | 7/1996 | Preti et al. |
| 5,574,179 A | 11/1996 | Wahl et al. |
| 5,576,282 A | 11/1996 | Miracle et al. |
| 5,597,936 A | 1/1997 | Perkins et al. |
| 5,651,976 A | 7/1997 | Price et al. |
| 6,103,678 A | 8/2000 | Masschelein et al. |
| 6,150,409 A | 11/2000 | Restrepo et al. |
| 6,225,464 B1 | 5/2001 | Hiler, II et al. |
| 6,326,348 B1 | 12/2001 | Vinson et al. |
| 6,413,920 B1 | 7/2002 | Bettiol et al. |
| 6,458,754 B1 | 10/2002 | Velazquez et al. |
| 6,488,943 B1 | 12/2002 | Beerse et al. |
| 6,531,444 B1 | 3/2003 | Shefer et al. |
| 7,018,978 B2 | 3/2006 | Miracle et al. |
| 7,119,060 B2 | 10/2006 | Shefer et al. |
| 7,223,361 B2 | 5/2007 | Kvietok et al. |
| 7,316,994 B2 | 1/2008 | Jordan, IV et al. |
| 7,365,043 B2 | 4/2008 | Baker et al. |
| 7,585,833 B2 | 9/2009 | Fadel et al. |
| 7,590,232 B2 | 9/2009 | Carter et al. |
| 7,722,807 B2 | 5/2010 | Keller, Jr. et al. |
| 7,763,238 B2 | 7/2010 | Preti et al. |
| 8,651,395 B2 | 2/2014 | Kvietok et al. |
| 8,986,717 B2 | 3/2015 | Franklin |
| 2004/0156742 A1 | 8/2004 | Milan et al. |
| 2005/0143282 A1 | 6/2005 | Creutz et al. |
| 2006/0003913 A1 | 1/2006 | Boutique et al. |
| 2006/0263313 A1 | 11/2006 | Scavone et al. |

(Continued)

FOREIGN PATENT DOCUMENTS

| | | |
|---|---|---|
| CN | 102362660 A | 2/2012 |
| GB | 1 589 755 A | 5/1981 |

(Continued)

OTHER PUBLICATIONS

Kodama et al, JP 2006-219413 Machine Translation, Aug. 24, 2006.*

(Continued)

Primary Examiner — Jessica E Whiteley
(74) Attorney, Agent, or Firm — Kathleen Y. Carter; Carrie M. Schwartz

(57) ABSTRACT

The present application relates to fragrance compositions comprising perfume raw materials that resist fragrance habituation, and methods for making and using the fragrance compositions.

7 Claims, No Drawings

(56) References Cited

U.S. PATENT DOCUMENTS

| | | | |
|---|---|---|---|
| 2007/0275866 A1 | 11/2007 | Dykstra | |
| 2008/0138441 A1 | 6/2008 | Schwartz et al. | |
| 2009/0324660 A1 | 12/2009 | Cetti et al. | |
| 2010/0308130 A1 | 12/2010 | Gruenbacher et al. | |
| 2011/0306538 A1* | 12/2011 | Joichi | A61K 8/37 512/10 |
| 2014/0170101 A1* | 6/2014 | Cetti | A61K 8/46 424/65 |
| 2014/0170102 A1* | 6/2014 | Cetti | A61K 8/46 424/65 |
| 2014/0170194 A1* | 6/2014 | Cetti | A61K 8/46 424/401 |
| 2014/0179722 A1* | 6/2014 | Cetti | A61K 8/46 514/277 |
| 2014/0179748 A1* | 6/2014 | Cetti | A61K 8/46 514/365 |

FOREIGN PATENT DOCUMENTS

| | | | |
|---|---|---|---|
| JP | 2003-137758 | * | 5/2003 |
| JP | 2005-170811 A | | 6/2005 |
| JP | 2006-219413 | * | 8/2006 |
| JP | 5016274 B2 | | 9/2012 |
| WO | 2008/149065 A1 | | 12/2008 |
| WO | 2014093748 | * | 12/2013 |
| WO | 2014093748 | * | 6/2014 |
| WO | 2014093828 | * | 6/2014 |

OTHER PUBLICATIONS

Kawasaki, JP 2003-137758 Machine Translation, May 14, 2003.*
PCT International Search Report and Written Opinon for PCT/US2013/074986 dated May 19, 2014.
Standard Practice for Determination of Odor and Taste Thresholds by a Forced-Choice Ascending Concentration Series Method of Limits, ASTM International, Designation: E679-04 (Reapproved 2011), pp. 1-7.
International Search Report and Written Opinion of the International Searching Authority PCT/US2015/029434 mailed Oct. 30, 2015, 26 pages.
Dalton et al., The nature and duration of adaptation following long-term odor exposure, Perception & Psychophysics 1996, 58(5), 781-792.

* cited by examiner

FRAGRANCE COMPOSITIONS

FIELD OF THE INVENTION

The present invention relates to the field of perfumery. In particular, the present invention relates to fragrance compositions, as well as methods for making and using such fragrance compositions that can reduce and/or eliminate consumer fragrance habituation.

BACKGROUND OF THE INVENTION

It has been a long tradition that highly skilled perfumers carefully select fragrance oils to blend into a fragrance composition in order to provide a desired and long-lasting fragrance or scent with each application. In so doing, they need to bear in mind differences in the individual character, volatility, and/or odour detection threshold of the fragrance materials that are the components of the full fragrance. Conventional perfuming compositions have fragrance profile characterized by the presence of low volatile fragrance materials and volatile fragrance materials. The low volatile fragrance materials are known as "base notes", while the volatile fragrance materials can be further divided into high volatile fragrance materials, identified as "top notes" or "head notes", and medium volatile fragrance materials, identified as "middle notes" or "heart notes".

The top notes tend to smell citrusy, green, light, fresh, and quickly evaporate due to their high volatility. Top notes are characterized by vapor pressure >0.1 Torr (Calculated using Advanced Chemistry Development (ACD/Labs) Software V11.02 ©1994-2013 ACD/Labs)). Middle notes are associated with floral aromas (e.g., jasmin, rose), fruity, marine or spicy aromas, and have an intermediate volatity in the vapor pressure range of 0.001 to 0.1 Tort Base or bottom notes are characterized as animalic, woody, sweet, amber or musky, not being very volatile, and having a vapor pressure <0.001 Torr.

In addition to the volatility, another important characteristic of a perfume raw material is its olfactory detection level. If a perfume raw material has a low odour detection threshold, otherwise known as "high odour impact", only very low levels are required of the perfume raw material within a fragrance composition for it to be detected by the user, sometimes as low as a few parts per billion (i.e., ≤50 ppb). Conversely, if a perfume raw material has a high odour detection threshold (i.e., ≥50 ppb), otherwise known as a "low odour impact", larger amounts of that material are required before it can be smelt by the user.

Conventional perfuming compositions can provide desirable scents initially, but over time consumers can become habituated to the perfume raw materials (PRMs) that form the fragrance. This means after a long period of time, the users and people around them can no longer detect the fragrance. Typically, the habituation problem can be found with perfume raw materials that are less volatile. That may be because the top notes are too volatile and linger around for so little time that the consumers do not have sufficient exposure to trigger the habituation effect. Whereas heart and base notes are on the skin and in the air around the consumer for long periods of time and therefore have ample time to induce habituation.

To overcome the habituation effect and allow consumers to continue to perceive the original scent, particularly over very long periods of time, consumers can: (1) use increasingly larger volumes of the fragrance composition; (2) continually re-apply the fragrance composition throughout the course of the day/evening, and/or (3) switch to a new fragrance composition containing different perfume oils for a significant period of time to reverse the habituation.

However, none of these solutions are particularly desirable. Option (1) can result in an an initial scent that is overpowering and possibly even offensive to the users and/or people around them. Option (2) tends to be costly and may not work since fragrance habituation of the perfume can lead to a diminished perception of the desired scent by the consumers, even when the quantity of the perfume material in the fragrance composition remains consistent and/or increases. The last solution is not particularly appealing either, especially, since many consumers have a signature perfume that they are known for and do not wish to switch.

Accordingly, there remains a need for an improved fragrance compositions that provide long-lasting and desirable scents that can reduce and/or eliminate the fragrance habituation effect in consumers, preferably over long periods of time. It is desirable that the solution to the habituation effect does not require consumers to modify their normal usage habits. It is further desirable to formulate a fragrance composition having improved longevity of the fragrance character, preferably components derived from the less volatile perfume raw materials (i.e., 0.1 to 0.001 Torr or ≤0.001 Torr) and/or having a low odour detection threshold (i.e., ≤50 ppb), preferably over long periods of time.

SUMMARY OF THE INVENTION

The Applicants have surprisingly discovered that perfume raw materials having certain chemical moieties are not subject to the fragrance habituation phenomenon. In a first aspect, the present invention is directed to a fragrance composition that includes a fragrance oil that comprises one or more perfume raw materials that resists fragrance habituation by a consumer to the composition. The perfume raw material is selected from the group consisting of: (a) from about 0.0000001% to about 10% of a perfume raw material comprising a thiol moiety; (b) from about 0.0000001% to about 10% of a perfume raw material comprising a sulfide moiety; (c) from about 0.000001% to about 10% of a perfume raw material comprising a thiazole moiety; (d) from about 0.0000001% to about 10% of a perfume raw material comprising an oxathiane moiety; (e) from about 0.000001% to about 10% of a perfume raw material comprising oxygen, sulfur, and nitrogen; (0 from about 0.00000005% to about 5% of a perfume raw material comprising a pyrazine moiety; (g) from about 0.00001% to about 20% of a perfume raw material comprising a nitrile moiety; (h) from about 0.000001% to about 10% of a perfume raw material comprising an indole moiety; (i) from about 0.00001% to about 10% of a perfume raw material comprising an oxime moiety; (j) from about 0.00001% to about 20% of a perfume raw material comprising an amine moiety; (k) from about 0.00000005% to about 5% of a perfume raw material comprising an isothiocyanate; (1) from about 0.00000005% to about 5% of a perfume raw material comprising a diamine moiety; and (m) mixtures thereof, with the proviso that the sum of the percentage of the perfume raw materials cannot exceed 100%.

In another aspect, the present invention relates to a method of resisting fragrance habituation of a fragrance composition by a consumer, the method comprising administering a fragrance composition as described herein above to the consumer.

One aim of the present invention is to provide a fragrance composition as described herein above which comprises perfume raw materials that can exhibit good fragrance anti-habituation properties, preferably over long periods of time at ambient conditions.

Another aim of the present invention is to provide such a fragrance composition as described herein above wherein the full fragrance "Odour Detection Threshold" remains substantively unchanged for the fragrance oils that contain perfume raw materials that resists the fragrance habituation of a consumer, preferably over long periods of time at ambient conditions.

A further aim of the present invention is to provide such a fragrance composition as described herein above wherein the perfume raw materials that resists the fragrance habituation of a consumer tend not to exhibit substantial decreases in the "Odour Detection Threshold" at ambient conditions after 2 hours, or after 4 hours, or after 6 hours, or after 8 hours, or after 10 hours, or after 12 hours, or intervals therein between or over long periods of time.

These and other features, aspects, and advantages of the present invention will become evident to those skilled in the art from the detailed description which follows.

DETAILED DESCRIPTION OF THE INVENTION

Definitions

As used herein, articles such as "a" and "an" when used in a claim, are understood to mean one or more of what is claimed or described.

As used herein, the terms "include", "includes" and "including" are meant to be non-limiting.

As used herein, the term "ambient" refers to surrounding conditions at about one atmosphere of pressure, 50% relative humidity and about 25 C.°.

As used herein, the term "fragrance composition" includes a fine fragrance composition intended for application to a body surface, such as for example, skin or hair, i.e., to impart a pleasant odour thereto, or cover a malodour thereof. They are generally in the form of perfume concentrates, perfumes, eau de parfums, eau de toilettes, aftershaves, colognes, body splashes, or body sprays. The fine fragrance compositions may be ethanol based compositions.

As used herein, the term "consumer" means both the user of the fragrance composition and the observer nearby or around the user.

As used herein, the terms "fragrance material" and "perfume raw material" are used interchangeably and relate to a perfume raw material, or a mixture of perfume raw materials, that are used to impart an overall pleasant odour or fragrance profile to a composition. "Fragrance materials" can encompass any suitable perfume raw materials for fragrance uses, including materials such as, for example, alcohols, aldehydes, ketones, esters, ethers, acetates, nitriles, terpene hydrocarbons, nitrogenous or sulfurous heterocyclic compounds and essential oils. However, naturally occurring plant and animal oils and exudates comprising complex mixtures of various chemical components are also know for use as "fragrance materials". The individual perfume raw materials which comprise a known natural oil can be found by reference to Journals commonly used by those skilled in the art such as "Perfume and Flavourist" or "Journal of Essential Oil Research", or listed in reference texts such as the book by S. Arctander, *Perfume and Flavor Chemicals*, 1969, Montclair, N.J., USA and more recently re-published by Allured Publishing Corporation Illinois (1994). Additionally, some perfume raw materials are supplied by the fragrance houses (Firmenich, International Flavors & Fragrances, Givaudan, Symrise) as mixtures in the form of proprietary specialty accords. Non-limiting examples of the fragrance materials useful herein include pro-fragrances such as acetal pro-fragrances, ketal pro-fragrances, ester pro-fragrances, hydrolyzable inorganic-organic pro-fragrances, and mixtures thereof. The fragrance materials may be released from the pro-fragrances in a number of ways. For example, the fragrance may be released as a result of simple hydrolysis, or by a shift in an equilibrium reaction, or by a pH-change, or by enzymatic release.

As used herein, the term "fragrance profile" means the description of how the fragrance perceived by the human nose evolves over time from when it is first applied. It is a result of the combination of the top, middle and base notes, if present, of a fragrance. A fragrance profile is composed of 2 characteristics: 'intensity' and 'character'. The 'intensity' relates to the perceived strength whilst 'character' refers to the odour impression or quality of the perfume, i.e., fruity, floral, woody, etc.

As used herein, the term "habituating" or "habituation" refers an individual or group who has decreased sensitivity to perceiving a fragrance or fragrance material. A fragrance or fragrance material is considered habituated when their Degree of Habituation (percent change in odor detection threshold or "ODT") is greater than 150%, greater than 300%, greater than 500%, greater than 1000% according to the method described in the Test Methods section of this specification.

As used herein, the term "long periods of time" refers to both 1) a period of time after a single use of the fragrance composition, which may consist of multiple applications on a given use occasion, anywhere from 2 hours, 3 hours, 4 hours, 5 hours, 6 hours, 7 hours, 8 hours, 9 hours, 10 hours, 11 hours, 12 hours, 24 hours up to and beyond 36 hours, and 2) the days, weeks and months over which a consumer may use a fragrance on a regular basis. "Regular basis" is defined as more than a single occasion in a 4 week period and maybe daily, every other day, 2-3 times per week, at weekends only or on a weekly basis.

As used herein, the terms "modulator" and "fixative" are used interchangeably to designate an agent having the capacity to affect the fragrance profile by impacting the fragrance materials' evaporation rate. By incorporating the modulator, it is desired that the fragrance profile, preferably the volatile fragrance materials components, of the composition can be perceived by an observer or user thereof, over a longer period of time, as compared to the same perception in the absence of the modulator. In particular, according to the invention, alkoxylated methyl glucoside, preferably PPG-20 Methyl Glucose Ether (Glucam™ P-20 available from Lubrizol (USA)), is a modulator of the perceived tenacity of the compositions of the present invention, i.e., it is used to prolong the perceived intensity of the fragrance profile over time, as compared to the perception when PPG-20 Methyl Glucose Ether is not used in the composition. However, as discovered by the inventors, simply adding modulators to a traditionally constructed fragrance composition will not ensure an improved or enhanced fragrance profile over time. Instead, it is only when the modulators are added in the presence of reduce levels of low volatile fragrance materials can the intensity of the fragrance profile, preferably the volatile fragrance materials, be perceived for longer periods as compared to control composition absent the modulators and low levels of low volatile fragrance materials.

As used herein, the term "co-modulator" means an agent that is added to the composition in addition to the modulators and has the similar function of impacting the evaporation rate and intensity of the fragrance materials, so as to improve or prolong the perception of the fragrance profile by the consumer. Preferred example of a co-modulator is isocetyl alcohol (CERAPHYL® ICA; see PCT Publication No. WO2013/64412 (Firmenich)).

As used herein, the term "non-odorous" means an agent that does not impart an odour of its own when added into a composition of the present invention. For example, a "non-odorous modulator" such as PPG-20 Methyl Glucose Ether does not impart a new odour that alters the character of the composition to which it is added.

As used herein, the term "Odour Detection Threshold" refers to the lowest vapour concentration of that material which can be olfactorily detected. The ODT is measured according to the method disclosed in the Test Method Section herein below.

As used herein, the terms "perfume" and "fragrance" are used interchangeably to designate the component in the composition that is formed of fragrance materials, i.e., ingredients capable of imparting or modifying the odour of skin or hair or other substrate. As used herein, the term "vapor pressure" means the partial pressure in air at a defined temperature for a given chemical species. It defines a chemical species' desire to be in the gas phase rather than the liquid or solid state. The higher the vapour pressure the greater the proportion of the material that will, at equilibrium, be found in a closed headspace. It is also related to the rate of evaporation of a fragrance material which is defined in an open environment where material is leaving the system. The vapor pressure is determined according to the reference program Advanced Chemistry Development (ACD/Labs) Software Version 11.02, (©1994-2013).

It is understood that the test methods that are disclosed in the Test Methods Section of the present application must be used to determine the respective values of the parameters of Applicants' inventions as described and claimed herein.

In all embodiments of the present invention, all percentages are by weight of the total composition, as evident by the context, unless specifically stated otherwise. All ratios are weight ratios, unless specifically stated otherwise, and all measurements are made at 25° C., unless otherwise designated.

Fragrance Compositions

The present invention is based on the surprising discovery that perfume raw materials having certain chemical moieties that are not susceptible to fragrance habituation. Specifically, in one aspect, the present invention is directed to a fragrance composition comprising one or more perfume raw materials (PRMs) such that the PRMs resist the fragrance habituation of a consumer to the fragrance composition.

In one embodiment, the fragrance composition comprises from about 0.01% to about 30%, or from about 0.1% to 25%, preferably from 0.5 to 20%, more preferably from 1% to 18%, even more preferably from 2% to 15% of the fragrance oil, or most preferably from 5% to 15%.

In another embodiment, the fragrance oil comprises one or more perfume raw materials, based on the total perfume weight, selected from the group consisting of:
  a) from about 0.0000001% to about 10%, from about 0.000001% to about 5%, from about 0.000005% to about 2.5%, from about 0.00001% to about 1%, from about 0.000025% to about 0.8%, of a perfume raw material comprising a thiol moiety;
  b) from about 0.0000001% to about 10%, from about 0.0000001% to about 5%, from about 0.000005% to about 2.5%, from about 0.00001% to about 1%, from about 0.000025% to about 0.5%, of a perfume raw material comprising a sulfide moiety;
  c) from about 0.000001% to about 10%, from about 0.000005% to about 5%, from about 0.00001% to about 2.5%, from about 0.0005% to about 1%, from about 0.001% to about 0.1%, of a perfume raw material comprising a thiazole moiety;
  d) from about 0.0000001% to about 10%, from about 0.000001% to about 5%, from about 0.000005% to about 2.5%, from about 0.00001% to about 1%, from about 0.000025% to about 0.8%, of a perfume raw material comprising an oxathiane moiety;
  e) from about 0.000001% to about 10%, from about 0.000005% to about 5%, from about 0.00001% to about 2.5%, from about 0.0005% to about 1%, from about 0.001% to about 0.1%, of a perfume raw material comprising oxygen, sulfur, and nitrogen;
  f) from about 0.00000005% to about 5%, from about 0.0000001% to about 2.5%, from about 0.0000005% to about 2%, from about 0.000001% to about 1%, from about 0.1% to about 2.5%, of a perfume raw material comprising a pyrazine moiety;
  g) from about 0.00001% to about 20%, from about 0.0001% to about 15%, from about 0.001% to about 10%, from about 00.01% to about 5%, from about 0.1% to about 2.5%, of a perfume raw material comprising a nitrile moiety;
  h) from about 0.000001% to about 10%, from about 0.00001% to about 7%, from about 0.0001% to about 4%, from about 0.001% to about 2%, from about 0.01% to about 1%, of a perfume raw material comprising an indole moiety;
  i) from about 0.00001% to about 10%, from about 0.0001% to about 7.5%, from about 0.001% to about 5%, from about 0.001% to about 2.5%, from about 0.01% to about 1%, of a perfume raw material comprising an oxime moiety;
  j) from about 0.00001% to about 20%, from about 0.0001% to about 15%, from about 0.001% to about 10%, from about 0.01% to about 5%, from about 0.1% to about 2.5%, of a perfume raw material comprising an amine moiety;
  k) from about 0.00000005% to about 5%, from about 0.0000001% to about 2.5%, from about 0.0000005% to about 2%, from about 0.000001% to about 1%, from about 0.000005% to about 0.5%, of a perfume raw material comprising an isothiocyanate;
  l) from about 0.00000005% to about 5%, from about 0.0000001% to about 2.5%, from about 0.0000005% to about 2%, from about 0.000001% to about 1%, from about 0.000005% to about 0.5%, of a perfume raw material comprising a diamine moiety; and
  m) mixtures thereof,
with the proviso that the sum of the percentage of the perfume raw materials cannot exceed 100%.

In another embodiment, the fragrance composition comprises one or more perfume raw materials selected from the group consisting of:
  a) a thiol moiety selected from the group consisting of 5-methyl-5-sulfanylhexan-3-one; 2-(4-methyl-1-cyclohex-3-enyl)propane-2-thiol; 5-methyl-2-(2-sulfanylpropan-2-yl)cyclohexan-1-one; 4,7,7-trimethyl-6-thiabicyclo[3.2.1]octane; 4-methoxy-2-methylbutane-2-thiol; methanethiol; ethanethiol; prop-2-ene-1-thiol; propane-2-thiol; 2-methylpropane-2-thiol; propane-1-thiol; butane-2-thiol; butane-1-thiol; 2-methylpropane-1-thiol; methyldisulfanylmethane; 2-methylbutane-2- thiol; 3-methylbutane-2-thiol; 3-methylbutane-2-thiol; pentane-2-thiol; pentane-1-thiol; 2-methylbutane-1-thiol; cyclopentanethiol; 3-methyldisulfanylprop-1-ene; methylsulfanyldisulfanylmethane; 1-methyldisulfanylpropane; ethane-1,2-dithiol; 1-(methyldisulfanyl) prop-1-ene; 3-sulfanylbutan-2-one; ethyldisulfanylethane; hexane-1-thiol; 1-ethyldisulfanylpropane; thiophene-2-thiol; propane-1,3-dithiol; 3-sulfanylpentan-2-one; 2-propan-2-yldisulfanylpropane; butane-1,4-dithiol; benzenethiol; ethylsulfanyldisulfanylethane; 3-methylsulfanyldisulfanylprop-1-ene; 1-methylsulfanyldisulfanylpropane; butane-2,3-dithiol; 4-methyl-4-sulfanylpentan-2-one; 3-prop-2-enyldisulfanylprop-1-ene; 1-methoxyhexane-3-thiol; ethyl 2-sulfanylpropanoate; 1-(prop-2-enyldisulfanyl)propane; 1-propyldisulfanylpropane; 1-(4-hydroxy-3-methoxyphenyl)ethanone butane-1,3-dithiol; 1-propyldisulfanylprop-1-ene; 2-methylbenzenethiol; thiophen-2-ylmethanethiol; 3-sulfanylbutan-2-ol; phenylmethanethiol pentane-1,5-dithiol; 2-ethylbenzenethiol; 3-prop-2-enylsulfanyldisulfanylprop-1-ene; methyldisulfanyldisulfanylmethane; 1-propyl sulfanyldisulfanylpropane; 2,7,7-trimethylbicyclo[3.1.1]heptane-2-thiol; 2,6-dimethylbenzenethiol; 2-phenylethanethiol; hexane-1,6-dithiol; 2-(methyldisulfanylmethyl)furan; pyridin-2-ylmethanethiol; 2-methoxybenzenethiol; (7,7-dimethyl-2-bicyclo[3.1.1]heptanyl)methanethiol; methyldisulfanylbenzene; 1-butyldisulfanylbutane; (4-methoxyphenyl)methanethiol; 2-sulfanylpropanoic acid; ethyl 2-methyldisulfanylpropanoate; (2E)-3,7-dimethylocta-2,6-diene-1-thiol; 3,7-dimethylocta-2,6-diene-1-thiol; pyrazin-2-ylmethanethiol; methyldisulfanylmethylbenzene; 2-methyl-5-(1-sulfanylpropan-2-yl)cyclohexane-1-thiol; octane-1,8-dithiol; 2-pyrazin-2-ylethanethiol; naphthalene-2-thiol; 2-oxo-3-sulfanylpropanoic acid; 2-thiophen-2-yldisulfanylthiophene; cyclohexyldisulfanylcyclohexane; 2-(furan-2-ylmethyldisulfanylmethyl)furan; phenyldisulfanylbenzene; benzyldisulfanylmethylbenzene; 8-Hydroxy-5-quinolinesulfonic acid; bis(3-methylbutyl) 2-sulfanylbutanedioate; 2-aminoethanesulfonic acid; 2-phenyl-3H-benzimidazole-5-sulfonic acid; 2-methyl-2-sulfanylpentan-1-ol; and mixtures thereof;

b) a sulfide moiety selected 1-butylsulfanylbutane; ethyl 3-methylsulfanylpropanoate; 2-(methylsulfanylmethyl)furan; methylsulfanylmethane; methylsulfanylethane; 3-methylsulfanylprop-1-ene; S-methyl ethanethioate; ethylsulfanylethane; 1-methylsulfanylpropane; S-ethyl ethanethioate; 1-methylsulfanylbutane; 2-propan-2-ylsulfanylpropane; bis(methylsulfanyl)methane; 1-ethylsulfanylpropane; thiolane; 1-propylsulfanylpropane; 1-ethylsulfanylbutane; S-ethyl propanethioate; S-methyl butanethioate; S-methyl 3-methylbutanethioate; 3-methylsulfanylpropanal; 3-prop-2-enylsulfanylprop-1-ene; methyl 2-methylsulfanylacetate; S-prop-2-enyl propanethioate; 1-methylsulfanylbutan-2-one; 4-methylsulfanylbutan-2-one; 3-methylsulfanylpropan-am; 2,4,6-trimethyl-1,3,5-trithiane; 3-methylsulfanylbutanal; 2-methyl-1,3-thiazolidine; 2-methyl-4,5-dihydro-1,3-thiazole; ethyl 2-methylsulfanylacetate; methyl 3-methylsulfanylpropanoate; S--propan-2-yl 3-methylbutanethioate; 4-methyl-4-methylsulfanylpentan-2-one; 2-methyl-1,3-dithiolane; methyl 2-methylsulfanylbutanoate; S-methyl furan-2-carbothioate; S-propan-2-yl 3-methylbut-2-enethioate; thiolan-3-one; 3,5-diethyl-1,2,4-trithiolane; methylsulfanylmethylbenzene; 3-methylsulfanylpropan-1-ol; 2-(propan-2-ylsulfanylmethyl)furan; 2-methyl-5-methylsulfanylfuran; S-(furan-2-ylmethyl) methanethioate; 1,2,4-trithiolane; 2-methylthiolan-3-one; 4-methylsulfanylbutan-1-ol; S-butan-2-yl 3-methylbutanethioate; S-butan-2-yl 3-methylbut-2-enethioate; S-(furan-2-ylmethyl) ethanethioate; 2-propyl-1,3-thiazolidine; 3-methyl-1,1-bis(methylsulfanyl)butane; 3-ethylsulfanylpropan-1-ol; S-methyl benzenecarbothioate; 3,5-dimethyl-1,2,4-trithiolane; S-butan-2-yl 2-methylbutanethioate; methylsulfanylbenzene; 1-pentylsulfanylpentane; (2R,4S)-2-methyl-4-propyl-1,3-oxathiane; 2-methyl-4-propyl-1,3-oxathiane; ethyl 2-methyl-2-methylsulfanylpropanoate; S-(furan-2-ylmethyl) propanethioate; 4,7,7-trimethyl-6-thiabicyclo[3.2.1]octane; 3-methyl-1,2,4-trithiane; methylsulfanylmethyl hexanoate; 1-(4,5-dihydro-1,3-thiazol-2-yl)ethanone; 3-methylsulfanylpropanoic acid; 5-methylsulfanyl-2-(methylsulfanylmethyl)pent-2-enal; 4,5-dimethyl-2-(2-methylpropyl)-2,5-dihydro-1,3-thiazole; 3-methylsulfanylhexan-1-ol; 2-methyl-4,5-dihydrofuran-3-thiol acetate; 4-(3-oxobutylsulfanyl)butan-2-one; 3-methylsulfanylbutanoic acid; 2-methylsulfanylpyrazine; 2-methyl-3-methylsulfanylpyrazine; 2-(furan-2-ylmethylsulfanylmethyl)furan; 2-(methylsulfanylmethyl)pyrazine; 3,5-di(propan-2-yl)-1,2,4-trithiolane; 2-methylsulfanylphenol; ethyl 3-(furan-2-ylmethylsulfanyl)propanoate; 2,2,4,4,6,6-hexamethyl-1,3,5-trithiane; 2-methyl-5,7-dihydrothieno[3,4-d]pyrimidine; 2-amino-4-methylsulfanylbutanoic acid; (2S)-2-amino-4-methylsulfanylbutanoic acid; 2',3a-dimethylspiro[6,6a-dihydro-5H-[1,3]dithiolo[4,5-b]furan-2,3'-oxolane]; 2,5-dimethyl-1,4-dithiane-2,5-diol; Methyl 2-thiofuroate; and mixtures thereof;

c) a thiazole moiety selected from the group consisting of 5-(2-hydroxyethyl)-4-methylthiazole; 2-(2-methylpropyl)-1,3-thiazole; 2-(4-methyl-1,3-thiazol-5-yl)ethanol; 4-methyl-2-propan-2-yl-1,3-thiazole; 1-(1,3-thiazol-2-yl)ethanone; 2,4,5-Trimethylthiazole; 2-isopropyl-4-methylthiazole; 4-vinyl-5-methylthiazole; 2,4-Dimethyl-5-acetylthiazole 1,3-thiazole; 4-methyl-1,3-thiazole; 2,4-dimethyl-1,3-thiazole; 4,5-dimethyl-1,3-thiazole; 2,5-dimethyl-1,3-thiazole; 5-ethenyl-4-methyl-1,3-thiazole; 2-ethyl-4-methyl-1,3-thiazole; 4-ethyl-2-methyl-1,3-thiazole; 2-propyl-1,3-thiazole; 2,4,5-trimethyl-1,3-thiazole; 2-ethyl-1,3-thiazole; 2-ethoxy-1,3-thiazole; 2-butan-2-yl-1,3-thiazole; 5-methoxy-2-methyl-1,3-thiazole; 2-ethyl-4,5-dimethyl-1,3-thiazole; 1,3-benzothiazole; 2,5-diethyl-4-methyl-1,3-thiazole; 1-(1,3-thiazol-2-yl)propan-1-one; 4,5-dimethyl-2-(2-methylpropyl)-1,3-thiazole; 2-methyl-1,3-benzothiazole; 1-(2,4-dimethyl-1,3-thiazol-5-yl)ethanone; 4-methyl-2-propan-2-yl-1,3-thiazole; and mixtures thereof;

d) an oxathiane moiety selected from the group consisting of (2R,4S)-2-methyl-4-propyl-1,3-oxathiane, 2-methyl-4-propyl-1,3-oxathiane, 2-pentyl-4-propyl-1,3-oxathiane; and mixtures thereof;

e) a moiety containing oxygen, sulfur, and nitrogen selected from the group consisting of 2-(4-methyl-1,3-thiazol-5-yl)ethanol; 1-(1,3-thiazol-2-yl)ethanone; 6-methyl-7-Oxa-1-thia-4-azaspiro[4.4]nonane; 2-[furan-2-ylmethyl]sulfanyl]-5-methylpyrazine; 2,4-Dimethyl-5-acetylthiazole; 2-ethoxy-1,3-thiazole; 5-methoxy-2-methyl-1,3-thiazole; 1-(4,5-dihydro-1,3- thiazol-2-yl)ethanone; 1-(1,3-thiazol-2-yl)propan-1-one; 1-(2,4-dimethyl-1,3-thiazol-5-yl)ethanone; 2-amino-4-methylsulfanylbutanoic acid; (2S)-2-amino-4-methylsulfanylbutanoic acid; 8-Hydroxy-5-quinolinesulfonic acid; 2-aminoethanesulfonic acid; 2-phenyl-3H-benzimidazole-5-sulfonic acid; and mixtures thereof.

f) a pyrazine moiety selected from the group consisting of 2-methoxy-3-(2-methylpropyl)pyrazine; 2,3-dimethylpyrazine; 1-pyrazin-2-ylethanone; 2-methyl-3-methylsulfanylpyrazine; Pyrazine; 2-methylpyrazine; 2-ethenylpyrazine; 2-ethylpyrazine; 2,6-dimethylpyrazine; 2,5-dimethylpyrazine; 2-prop-1-en-2-ylpyrazine; 2-propan-2-ylpyrazine; 2-methoxypyrazine; 2-ethenyl-5-methylpyrazine; 2-ethyl-5-methylpyrazine; 2-Ethyl-6-methylpyrazine; 2-Ethyl-3-Methyl-Pyrazine; 2-propylpyrazine; 2,3,5-trimethylpyrazine; 2-tert-butylpyrazine; pyrazin-2-amine; 2-(2-methylpropyl)pyrazine; 2-methyl-5-propan-2-ylpyrazine; 2-(methoxymethyl)pyrazine; 2,3-diethylpyrazine; 2-ethyl-3,(5 OR 6)-dimethylpyrazine; 2-ethyl-3,5-dimethylpyrazine; 3-ethyl-2,5-dimethylpyrazine; 3-ethyl-2,5-dimethylpyrazine; 2-ethyl-3,5-dimethylpyrazine; 2-methyl-3-propylpyrazine; 2,3,5,6-tetramethylpyrazine; 7-methyl-6,7-dihydro-5H-cyclopenta[b]pyrazine; 2-methylsulfanylpyrazine; 2-methyl-3-methylsulfanylpyrazine; 2-ethoxy-3-ethylpyrazine; 2-Isobutyl-3-methylpyrazine; pyrazin-2-ylmethanethiol; 3,5-dimethyl-2-propylpyrazine; 2-ethyl-3-methoxypyrazine; 2-ethoxy-3-methylpyrazine; 2-ethyl-5-methoxypyrazine; 5,6,7,8-tetrahydroquinoxaline; 2-ethoxy-3-propan-2-ylpyrazine; 2-(methylsulfanylmethyl)pyrazine; 3,5-dimethyl-2-(2-methylpropyl)pyrazine; 2,3-diethyl-5-methylpyrazine; 3,5-Diethyl-2-methylpyrazine; 2,5-dimethyl-3-(2-methylpropyl)pyrazine; 2-methyl-6-propoxypyrazine; 2-(2-methylpropoxyl)pyrazine; 1-(3-methylpyrazin-2-yl)ethanone; 2-methyl-3-methylsulfanylpyrazine; 2-methoxy-3-propan-2-ylpyrazine; quinoxaline; 3-butyl-2,5-dimethylpyrazine; 2-butyl-3,5-dimethylpyrazine; 2-pyrazin-2-ylethanethiol; 1-(3-ethylpyrazin-2-yl)ethanone; 1-(3,5-dimethylpyrazin-2-yl)ethanone; 2-butan-2-yl-3-methoxypyrazine; 2-methylquinoxaline; 5-Methylquinoxaline; 2-methoxy-3-(4-methylpentyl)pyrazine; 2,3-dimethylquinoxaline; 2-(cyclohexylmethyl)pyrazine; 2-[(furan-2-ylmethyl)sulfanyl]-5-methylpyrazine and mixtures thereof;

g) a nitrile moiety selected from the group consisting of 3,7-dimethyloct-6-enenitrile, 3-(4-ethylphenyl)-2,2-dimethylpropanenitrile; and mixtures thereof;

h) an indole moiety selected from the group consisting of 1H-indole, 3-methyl-1H-indole; and mixtures thereof;

i) an oxime moiety selected from the group consisting of (NE)-N-[(6E)-2,4,4,7-tetramethylnona-6,8-dien-3-ylidene]hydroxylamine; N-(5-methylheptan-3-ylidene)hydroxylamine, and mixtures thereof; and j) an amine moiety selected from the group consisting of methyl 2-aminobenzoate, pentane-1,5-diamine; 6-methyl-7-Oxa-1-thia-4-azaspiro[4.4]nonane; and mixtures thereof.

In yet another embodiment, the fragrance composition comprises one or more perfume raw materials selected from the group consisting of:

a) a thiol moiety selected from the group consisting of 5-methyl-5-sulfanylhexan-3-one; 2-(4-methyl-1-cyclohex-3-enyl)propane-2-thiol; 5-methyl-2-(2-sulfanylpropan-2-yl)cyclohexan-1-one; 4,7,7-trimethyl-6-thiabicyclo[3.2.1]octane; 4-methoxy-2-methylbutane-2-thiol; and mixtures thereof;

b) a sulfide moiety selected from the group consisting 1-butylsulfanylbutane; methylsulfanylmethane; ethyl 3-methylsulfanylpropanoate; 2-(methylsulfanylmethyl)furan; and mixtures thereof;

c) a thiazole moiety selected from the group consisting of 5-(2-hydroxyethyl)-4-methylthiazole; 2-(2-methylpropyl)-1,3-thiazole; 2-(4-methyl-1,3-thiazol-5-yl)ethanol; 4-methyl-2-propan-2-yl-1,3-thiazole; 4-methyl-2-propan-2-yl-1,3-thiazole; 1-(1,3-thiazol-2-yl)ethanone; and mixtures thereof;

d) an oxathiane moiety that is (2R,4S)-2-methyl-4-propyl-1,3-oxathiane; and e) a moiety containing oxygen, sulfur and nitrogen selected from the group consisting of 2-(4-methyl-1,3-thiazol-5-yl)ethanol, 1-(1,3-thiazol-2-yl)ethanone; 6-methyl-7-Oxa-1-thia-4-azaspiro[4.4]nonane; and mixtures thereof.

In yet another embodiment, the fragrance composition comprises one or more perfume raw materials selected from the group consisting of:

f) a pyrazine moiety is selected from the group consisting of 2-methoxy-3-(2-methylpropyl)pyrazine; 2,3-dimethylpyrazine; 1-pyrazin-2-ylethanone; 2-methyl-3-methylsulfanylpyrazine; and mixtures thereof;

g) a nitrile moiety is selected from the group consisting of 3,7-dimethyloct-6-enenitrile; 3-(4-ethylphenyl)-2,2-dimethylpropanenitrile; and mixtures thereof;

h) an indole moiety is selected from the group consisting of 1H-indole;

i) an oxime moiety is selected from the group consisting of (NE)-N-[(6E)-2,4,4,7-tetramethylnona-6,8-dien-3-ylidene]hydroxylamine; and j) an amine moiety is selected from the group consisting of methyl 2-aminobenzoate; pentane-1,5-diamine; 6-methyl-7-Oxa-1-thia-4-azaspiro[4.4]nonane; and mixtures thereof.

In yet another embodiment, the fragrance composition comprises one or more perfume raw materials selected from the group consisting of: 2-methyl-3-methylsulfanyl pyrazine; (NE)-N-[(6E)-2,4,4,7-tetramethylnona-6,8-dien-3-ylidene]hydroxylamine; 1-butylsulfanyl butane; 1-methylsulfanyl; and 5-(2-hydroxyethyl)-4-methylthiazole.

In yet another embodiment, the fragrance composition comprises one or more perfume raw materials comprising at least one sulfur, oxygen and nitrogen. Preferably, the perfume raw material is selected from the group consisting of 2-(4-methyl-1,3-thiazol-5-yl)ethanol; 1-(1,3-thiazol-2-yl)ethanone; 6-methyl-7-Oxa-1-thia-4-azaspiro[4.4]nonane; 2-[(furan-2-ylmethyl)sulfanyl]-5-methylpyrazine; 2,4-Dimethyl-5-acetylthiazole; 2-ethoxy-1,3-thiazole; 5-methoxy-2-methyl-1,3-thiazole; 1-(4,5-dihydro-1,3-thiazol-2-yl)ethanone; 1-(1,3-thiazol-2-yl)propan-1-one; 1-(2,4-dimethyl-1,3-thiazol-5-yl)ethanone; 2-amino-4-methylsulfanylbutanoic acid; (2S)-2-amino-4-methylsulfanylbutanoic acid; 8-Hydroxy-5-quinolinesulfonic acid; 2-aminoethanesulfonic acid; 2-phenyl-3H-benzimidazole-5-sulfonic acid; and mixtures thereof.

While not wishing to be bound by theory, Applicants believe that habituation is a phenomenon that is grounded in the consumer's physiology, in that the body is attempting to avoid having its sense of smell from being overwhelmed by any one stimulus after repeated chronic exposure to the stimulus. As such, habituation is likely a darwanian mechanism that has evolved over time. However, certain odours associated with danger and/or conditions that may be detrimental to or important in sustaining life are not subject to the habituation phenomenon. As a result, Applicants looked to odours that may be associated with danger and/or life essential conditions as Applicants believed that the evolutionary path of those who became habituated to such odours would have been cut short.

Surprisingly, Applicants have identified certain chemical moities that are associated with conditions that may be detrimental to or important in sustaining life. Based on this recognition, Applicants identified chemical moieties that are therefore not susceptible to fragrance habituation, and corresponding perfume raw materials comprising such chemical moieties. Accordingly, Applicants believe that fragrance compositions can resist fragrance habituation by incorporating perfume raw materials having these chemical moieties. Additionally, Applicants developed processes for making and using such fragrance compositions that are not susceptible to fragrance habituation.

Many consumers prefer fragrance compositions that can consistently provide a desired scent, or fragrance, that can be perceived upon application of the product and preferably for a long period of time thereafter. Habituation of the perfume raw materials by the consumer, however, can lead to a diminished perception of the desired scent, even when the quantity of perfume raw materials in the fragrance composition remains consistent and/or increases.

In yet another embodiment, a fragrance composition of the present invention can exhibit a fragrance anti-habituating effect on a consumer as having, for example:
 a) a two week anti-habituation index of at least 0, 1, 2, 3 or 4;
 b) a four week anti-habituation index of at least 0, 1, 2, 3, or 4;
 c) a two week anti-habituation index of 0, 1, 2, 3 or 4; and/or
 d) a four week anti-habituation index of 0, 1, 2, 3 or 4

In another aspect, fragrance oils may comprise many different types of perfume raw materials. Each perfume raw material differs from another by several important properties including individual character, volatility, and olfactory detection level. By bearing in mind these different properties, and others, the perfume raw materials can be blended to develop a fragrance composition with an overall desirable and long-lasting specific character profile.

For example, the less volatile and more substantive perfume raw materials are typically used to give animalic, woody, sweet, amber or musky characters. They may be detected soon after application and also last longer than more volatile PRMs. However, due to the habituation effect as noted above, the users cease to notice their scents after a period of time (e.g., after 2 hrs from application), especially over long period of time.

Accordingly, the Applicants believe that certain less volatile perfume raw materials can be incorporated into a fragrance composition to resist the habituating effect. Therefore, in another embodiment, the perfume raw materials disclosed herein present in the fragrance composition are selected from: (i) perfume raw materials having a chemical moiety selected from the group consisting of: a thiol moiety, a sulfide moiety, a thiazole moiety, an ozathiane moiety, a pyrazine moiety, an indole moiety, an oxime moiety, an amine moiety, an isothiocyanate moiety, a diamine moiety, compounds comprising oxygen, sulfur and nitrogen, and mixtures thereof; and (ii) wherein the perfume raw materials have a vapor pressure of less than 0.1 Torr, or 0.1 to 0.001 Torr, or less than 0.001 Torr.

In addition to volatility, olfactory detection level, otherwise known as the odour detection threshold of perfume raw materials is an important property that can influence fragrance habituation. For example, if a perfume raw material has a low odour detection threshold, otherwise known as "high odour impact", then very low levels of the perfume raw materials (i.e., ≤50 ppb) can be easily detectable by the consumers. However, due to the habituation effect as noted above, the users cease to notice their scents after a short period (e.g., after 2 hrs from application).

Accordingly, the Applicants believe that certain low odour detection threshold perfume raw materials can be incorporated into a fragrance composition to resist the habituating effect. Therefore, in another embodiment, the perfume raw materials disclosed herein present in the fragrance composition are selected from: (i) perfume raw materials having a chemical moiety selected from the group consisting of: a thiol moiety, a sulfide moiety, a thiazole moiety, an ozathiane moiety, a pyrazine moiety, an indole moiety, an oxime moiety, an amine moiety, an isothiocyanate moiety, a diamine moiety, compounds comprising oxygen, sulfur and nitrogen, and mixtures thereof; and (ii) wherein the perfume raw materials have an odour detection threshold of less than 50 parts per billion (ppb).

Fragrance Modulators

In one aspect, the perfume composition may contain a fragrance modulator. Fragrance modulators enhance intensity of a fragrance profile over time, preferably so that the volatile fragrance materials remain significantly consistent from its initial impression to the end. Fragrance modulators are disclosed in U.S. Provisional Patent Ser. No. 61/915,514 (P&G) which is incorporated by reference.

Thus, in one embodiment, the fragrance composition comprises:
 a) a fragrance component present in an amount of from about 1% to about 30%, preferably less than about 20%, preferably less than about 15%, preferably less than about 10% or preferably less than 8%, relative to the total weight of the composition; and wherein:
  (i) the fragrance component comprises at least one low volatile fragrance material having a vapor pressure less than 0.001 Torr; and
  (ii) the low volatile fragrance material is present in an amount of from about 0.1 wt % to about 30 wt %, preferably less than about 25 wt %, preferably less than about 22 wt %, preferably less than 20 wt %, preferably less than 18 wt %, preferably less than 15 wt %, or preferably less than about 12%, relative to the total weight of the fragrance component;
 b) at least one non-odorous fragrance modulator formed of an alkoxylated methyl glucoside selected from the group consisting of methyl glucoside polyol, ethyl glucoside polyol, and propyl glucoside polyol, preferably PPG-20 Methyl Glucose Ether, in an amount of from about 0.1% to about 20%, preferably about 0.5% to about 18%, or more preferably about 2.5% to about 15%, relative to the total weight of the composition.

In another embodiment, the low volatile fragrance material is selected from the group consisting of: 2-Buten-1-ol, 2-methyl-4-(2,2,3-trimethyl-3-cyclopenten-1-yl)-; Ethanone, 1-(2-naphthalenyl)-; 3-Decanone, 1-hydroxy-; Cyclopropanemethanol, 1-methyl-2-[(1,2,2-trimethylbicyclo[3.1.0]hex-3-yl)methyl]-; Benzaldehyde, 3-ethoxy-4-hydroxy-; 2H-1,5-Benzodioxepin-3(4H)-one, 7-methyl-; 2-Butanol, 1-[[2-(1,1-dimethylethyl)cyclohexyl]oxy]-; Spiro[5.5]undec-8-en-1-one, 2,2,7,9-tetramethyl-; Cyclopentaneacetic acid, 3-oxo-2-pentyl-, methyl ester, (1R,2R)- rel-; Cyclopentaneacetic acid, 3-oxo-2-pentyl-, methyl ester; Octanal, 2-(phenylmethylene)-; Indeno[4,5-d]-1,3-dioxin, 4,4a,5,6,7,8,9,9b-octahydro-7,7,8,9,9-pentamethyl-; Cyclopentanecarboxylic acid, 2-hexyl-3-oxo-, methyl ester; 3-Cyclopentene-1-butanol, α,β,2,2,3-pentamethyl-; Cyclopentanone, 2-(3,7-dimethyl-2,6-octadien-1-yl)-; 1,6,10-Dodecatrien-3-ol, 3,7,11-trimethyl-; 2-Pentenenitrile, 3-methyl-5-phenyl-, (2Z)—; Benzenepropanenitrile, 4-ethyl-α,α-dimethyl-; 1H-3a,7-Methanoazulen-6-ol, octahydro-3,6,8,8-tetramethyl-, (3R,3aS,6R,7R,8aS)—; Ethanone, 1-(1,2,3,5,6,7,8,8a-octahydro-2,3,8,8-tetramethyl-2-naphthalenyl)-; Ethanone, 1-(1,2,3,4,5,6,7,8-octahydro-2,3,8,8-tetramethyl-2-naphthalenyl)-; Propanoic acid, 2-methyl-, 4-formyl-2-methoxyphenyl ester; 1,6-Heptadien-3-one, 1-(2,6,6-trimethyl-2-cyclohexen-1-yl)-; Benzoic acid, 2-hydroxy-, hexyl ester; Benzoic acid, phenyl ester; Cyclohexanepropanol, 2,2,6-trimethyl-α-propyl-, (1R,6S)—; Cyclohexanepropanol, 2,2,6-trimethyl-α-propyl-; Benzoic acid, 2-hydroxy-, 3-methyl-2-buten-1-yl ester; 2H-1,5-Benzodioxepin-3(4H)-one, 7-(1-methylethyl)-; Butanal, 4-(octahydro-4,7-methano-5H-inden-5-ylidene)-; Cyclopenta[g]-2-benzopyran, 1,3,4,6,7,8-hexahydro-4,6,6,7,8,8-hexamethyl-; Cyclopentanone, 2-[2-(4-methyl-3-cyclohexen-1-yl)propyl]-; 2 (3H)-Naphthalenone, 4,4a,5,6,7,8-hexahydro-4,4a-dimethyl-6-(1-methylethenyl)-, (4R,4aS, 6R)—; 2-Propenoic acid, 3-phenyl-, pentyl ester; 4H-Pyran-4-one, 3-hydroxy-2-methyl-; 1-Propanol, 2-methyl-3-[(1,7,7-trimethylbicyclo[2.2.1]hept-2-yl)oxy]-; 1-Naphthalenol, 1,2,3,4,4a,5,8,8a-octahydro-2,2,6,8-tetramethyl-; 2-Butenoic acid, 2-methyl-, (2E)-3,7-dimethyl-2,6-octadien-1-yl ester, (2E)-; 1,3-Dioxane, 2-(2,4-dimethyl-3-cyclohexen-1-yl)-5-methyl-5-(1-methylpropyl)-; 4-Penten-2-ol, 3-methyl-5-(2,2,3-trimethyl-3-cyclopenten-1-yl)-; Propanoic acid, 2-methyl-, 2-methyl-4-oxo-4H-pyran-3-yl ester; 2-Buten-1-ol, 2-ethyl-4-(2,2,3-trimethyl-3-cyclopenten-1-yl)-; 1,6-Methanonaphthalen-1(2H)-ol, octahydro-4,8a,9,9-tetramethyl-, (1R,4S,4aS,6R,8aS)—; 2H-1,5-Benzodioxepin-3(4H)-one, 7-(1,1-dimethylethyl)-; Benzoic acid, phenylmethyl ester; 8-Cyclohexadecen-1-one; Benzoic acid, 2-hydroxy-, (3Z)-3-hexen-1-yl ester; 4H-Pyran-4-one, 2-ethyl-3-hydroxy-; Cyclopentadecanone, 3-methyl-; Benzoic acid, 2-hydroxy-, phenylmethyl ester; 6,8-Nonadien-3-one, 2,4,4,7-tetramethyl-, oxime; Benzoic acid, 2-hydroxy-, cyclohexyl ester; Benzene, [2-(dimethoxymethyl)-1-hepten-1-yl]-; 3-Cyclopentene-1-butanol, β,2,2,3-tetramethyl-δ-methylene-; 4-Penten-1-one, 1-spiro[4.5]dec-7-en-7-yl-; Acetic acid, 2-(1-oxopropoxy)-, 1-(3,3-dimethylcyclohexyl) ethyl ester; 4-Penten-2-ol, 3,3-dimethyl-5-(2,2,3-trimethyl-3-cyclopenten-1-yl)-; 5,8-Methano-2H-1-benzopyran-2-one, 6-ethylideneoctahydro-; 4-Cyclopentadecen-1-one, (4Z)—; Ethanone, 1-[(3R,3 aR,7R,8aS)-2,3,4,7,8,8a-hexahydro-3,6,8,8-tetramethyl-1H-3a,7-methano azulen-5-yl]-; 1,3-Dioxolane, 2,4-dimethyl-2-(5,6,7,8-tetrahydro-5,5,8,8-tetramethyl-2-naphthalenyl)-; Oxacyclohexadecan-2-one; 1-Propanol, 2-[1-(3,3-dimethylcyclohexyl)ethoxy]-2-methyl-, 1-propanoate; 5-Cyclopentadecen-1-one, 3-methyl-; 2H-1,5-Benzodioxepin-3(4H)-one, 7-(3-methylbutyl)-; Ethanone, 1-(2,6,10-trimethyl-2,5,9-cyclododecatrien-1-yl)-; 1H-3a,6-Methano azulene-3-methanol, octahydro-7,7-dimethyl-8-methylene-, (3S,3aR,6R,8aS)—; Benzeneacetonitrile, α-cyclohexylidene-; Benzoic acid, 2-[(2-methylpentylidene)amino]-, methyl ester; Benzoic acid, 2-phenylethyl ester; Cyclohexanol, 4-(1,7,7-trimethylbicyclo[2.2.1]hept-2-yl)-; 3-Cyclohexene-1-carboxaldehyde, 4-(4-hydroxy-4-methylpentyl)-; Ethanone, 1-(5,6,7,8-tetrahydro-3,5,5,6,8,8-hexamethyl-2-; 2-Cyclopentadecen-1-one, 3-methyl-; Oxacycloheptadecan-2-one; Benzeneacetic acid, 4-methylphenyl ester; Benzeneacetic acid, 2-phenylethyl ester; Cyclododecaneethanol, (3-methyl-; 2-Propenoic acid, 3-phenyl-, phenylmethyl ester; Benzoic acid, 2,4-dihydroxy-3,6-dimethyl-, methyl ester; Naphtho[2,1-b]furan-6(7H)-one, 8,9-dihydro-1,5,8-trimethyl-, (8R)—; Benzeneacetic acid, (4-methoxyphenyl) methyl ester; Benzene, 2-methoxy-1-(phenylmethoxy)-4-(1-propen-1-yl)-; Benzeneacetic acid, (2E)-3,7-dimethyl-2,6-octadien-1-yl ester; Benzoic acid, 2-hydroxy-, 2-phenylethyl ester; 2-Propenoic acid, 3-phenyl-, 1-ethenyl-1,5-dimethyl-4-hexen-1-yl ester; Oxacycloheptadec-10-en-2-one; Oxacycloheptadec-8-en-2-one, (8Z)—; 1,7-Dioxacycloheptadecan-8-one; 1,4-Dioxacyclohexadecane-5,16-dione; 1,4-Dioxacycloheptadecane-5,17-dione; Benzoic acid, 2-[(1-hydroxy-3-phenylbutyl)amino]-, methyl ester; and combinations thereof.

In another embodiment, the fragrance component comprises one or more volatile fragrance materials, wherein:
a) the volatile fragrance material has a vapor pressure ≥0.001 Torr;
b) the volatile fragrance material is present in an amount of from about 70% to about 99.9%, preferably greater than about 80%, or most preferably greater than about 88%, relative to the total weight of the fragrance component; and
c) combinations thereof.

In another embodiment, the volatile fragrance material is selected from the group consisting of:
a) a high volatile fragrance material having a vapor pressure >0.1 Torr;
b) a moderate volatile fragrance material having a vapor pressure in the range of 0.1 Torr to 0.001 Torr; and
c) combinations thereof.

In one embodiment, the volatile fragrance material is selected from the group consisting of: Formic acid, methyl ester; Methane, 1,1'-thiobis-; Acetic acid ethyl ester; Propanoic acid, ethyl ester; Acetic acid, 2-methylpropyl ester; Butanoic acid, ethyl ester; 1-Butanol; Butanoic acid, 2-methyl-, ethyl ester; 1-Butanol, 3-methyl-, 1-acetate; Butanoic acid, 2-methyl-, 1-methylethyl ester; 2-Heptanone; 2-Hexenal, (2E)-; 1-Butanol, 3-methyl-; 2-Buten-1-ol, 3-methyl-, 1-acetate; 1,3-Dioxolane-2-methanamine, N-methyl-; Bicyclo[3.1.1]hept-2-ene, 2,6,6-trimethyl-, (1R,5R)—; Bicyclo[2.2.1]heptane, 2,2-dimethyl-3-methylene-; 2-Butanethiol, 4-methoxy-2-methyl-; Pentanoic acid, 2-methyl-, ethyl ester; Bicyclo[3.1.1]heptane, 6,6-dimethyl-2-methylene-; 1-Butanol, 3-methyl-, 1-propanoate; 1,6-Octadiene, 7-methyl-3-methylene-; Octanal; 2H-Pyran, 2-ethenyltetrahydro-2,6,6-trimethyl-; 2-Octanone; Hexanoic acid, ethyl ester; 2-Oxabicyclo[2.2.2]octane, 1,3,3-trimethyl-; Benzene, 1-methyl-4-(1-methylethyl)-; Benzene, 1-methoxy-4-methyl-; 1,3,6-Octatriene, 3,7-dimethyl-; Cyclohexene, 1-methyl-4-(1-methylethenyl)-; Cyclohexene, 1-methyl-4-(1-methylethenyl)-, (4R)—; 3-Octanone; Undecanal, 2-methyl-; Acetic acid, hexyl ester; 5-Hepten-2-one, 6-methyl-; 2-Hepten-4-one, 5-methyl-; 3-Hexen-1-ol, 1-acetate, (3Z)—; 3-Hexen-1-ol, 1-acetate; Propanoic acid, 2-hydroxy-, ethyl ester; Butanoic acid, 2-methylbutyl ester; Butanoic acid, 3-methylbutyl ester; 1,4-Cyclohexadiene, 1-methyl-4-(1-methylethyl)-; Thiazole, 2-(2-methylpropyl)-; 3-Hexen-1-ol, (3Z)—; Benzaldehyde; Butanoic acid, 3-oxo-, ethyl ester; 2-Hexen-1-ol, (2E)-; 2-Hexen-1-ol, (2Z)—; Cyclohexane, 3-ethoxy-1,1,5-trimethyl-, cis-(9CI); 2-Pentanone, 4-mercapto-4-methyl-; 2,4,6-Octatriene, 2,6-dimethyl-, (4E,6E)-; Oxirane, 2,2-dimethyl-3-(3-methyl-2,4-pentadien-1-yl)-; 4,7-Octadienoic acid, methyl ester, (4E)-; Carbonic acid, (3Z)-3-hexen-1-yl methyl ester;

Hexanoic acid, 2-propen-1-yl ester; 5-Heptenal, 2,6-dimethyl-; Heptanoic acid, ethyl ester; 3-Cyclohexene-1-carboxaldehyde, 2,4-dimethyl-; Benzene, (2,2-dimethoxyethyl)-; 2H-Pyran, tetrahydro-4-methyl-2-(2-methyl-1-propen-1-yl)-; 3-Nonanone; Benzonitrile; 3-Octanol; 1-Hexanol, 3,5,5-trimethyl-, 1-acetate; 4-Heptanol, 2,6-dimethyl-, 4-acetate; Hexanoic acid, 2-methylpropyl ester; Propanoic acid, 2-methyl-, hexyl ester; Cyclohexanecarboxylic acid, 1,4-dimethyl-, methyl ester, trans-; Benzeneacetaldehyde; Butanoic acid, 3-hydroxy-, ethyl ester; Propanedioic acid, 1,3-diethyl ester; Benzoic acid, methyl ester; 1,3,5-Undecatriene; 4-Decenal, (4E)-; 1,3-Dioxane, 2-butyl-4,4,6-trimethyl-; 2-Heptanol, 2,6-dimethyl-; Ethanone, 1-phenyl-; Benzeneacetaldehyde, α-methyl-; Propanoic acid, 2-methyl-, 1,3-dimethyl-3-buten-1-yl ester; 2,6-Nonadienal, (2E,6Z)—; Pyrazine, 2-methoxy-3-(2-methylpropyl)-; Formic acid, phenylmethyl ester; Benzene, 1-methoxy-4-propyl-; Cyclohexanone, 5-methyl-2-(1-methylethyl)-, (2R,5R)-rel-; Cyclohexanone, 5-methyl-2-(1-methylethyl)-, (2R,5S)-rel-; 2-Nonenal; Cyclohexanone, 2-ethyl-4,4-dimethyl-; Benzene, 1,4-dimethoxy-; Benzene, 1-(ethoxymethyl)-2-methoxy-; Bicyclo[2.2.1]heptan-2-one, 1,7,7-trimethyl-; 2-Hexene, 6,6-dimethoxy-2,5,5-trimethyl-; Decanal; Benzenepropanal, (3-methyl-; Benzenemethanol, α-methyl-, 1-acetate; Acetic acid, nonyl ester; Ethanone, 1-(4-methylphenyl)-; 2H-Pyran, 6-butyl-3,6-dihydro-2,4-dimethyl-; Propanoic acid, 2-methyl-, (3Z)-3-hexen-1-yl ester; Benzoic acid, ethyl ester; 3-Octanol, 3,7-dimethyl-, 3-acetate; 1-Hexanol, 5-methyl-2-(1-methylethyl)-, 1-acetate; Cyclohexanol, 3,3,5-trimethyl-, (1R,5R)-rel-; 2-Hexenal, 5-methyl-2-(1-methylethyl)-; 7-Octen-2-ol, 2,6-dimethyl-; Acetic acid, phenylmethyl ester; Cyclohexanone, 2-(1-methylpropyl)-; 3-Octen-1-ol, (3Z)—; Heptanoic acid, 2-propen-1-yl ester; Benzenemethanol; Butanoic acid, 2-methyl-, hexyl ester; 2(3H)-Furanone, 5-ethyldihydro-; Cyclohexaneethanol, 1-acetate; 2-Nonenoic acid, methyl ester; Cyclohexanecarboxylic acid, 2,2-dimethyl-6-methylene-, methyl ester; Butanoic acid, (3Z)-3-hexen-1-yl ester; 2-Octynoic acid, methyl ester; 1,3-Oxathiane, 2-methyl-4-propyl-, (2R, 4S)-rel-; Heptanal, 6-methoxy-2,6-dimethyl-; Bicyclo[2.2.1]heptan-2-ol, 1,3,3-trimethyl-, 2-acetate; 1,6-Octadien-3-ol, 3,7-dimethyl-, 3-acetate; 2-Octanol, 2,6-dimethyl-; 1-Octanol; 3-Cyclohexene-1-methanethiol, α,α,4-trimethyl-; Cyclohexanemethanol, α,α,4-trimethyl-, 1-acetate; Cyclohexanol, 2-(1,1-dimethylethyl)-, 1-acetate; Cyclohexanol, 4-(1,1-dimethylethyl)-, 1-acetate; Pyrazine, 2-methoxy-3-(1-methylpropyl)-; Cyclohexanol, 5-methyl-2-(1-methylethenyl)-, (1R,2S,5R)—; 2-Undecanone; Benzenepropanol, α,α-dimethyl-; Bicyclo[2.2.1]heptan-2-ol, 1,7,7-trimethyl-, 2-acetate, (1R,2R,4R)-rel-; 1,6-Octadien-3-ol, 3,7-dimethyl-; Benzeneacetic acid, ethyl ester; Benzeneethanol, α,α-dimethyl-; Cyclopropanecarboxylic acid, (3Z)-3-hexen-1-yl ester; 3-Cyclohexene-1-methanol, 3,5-dimethyl-, -dimethyl-1-acetate; Undec anal; Ethanone, 1-(3-cycloocten-1-yl)-; Cyclohexanone, 4-(1,1-dimethylethyl)-; 6-Nonen-1-ol, (6Z)—; Benzene, (2-butoxyethyl)-; Cyclohexanecarboxylic acid, 2,2,6-trimethyl-, ethyl ester, (1R, 6S)-rel-; Benzeneethanol; 2,6-Octadienal, 3,7-dimethyl-, (2Z)—; 2,6-Octadienal, 3,7-dimethyl-; Cyclohexanol, 5-methyl-2-(1-methylethyl)-, 1-acetate, (1R,2S,5R)-rel-; Benzoic acid, 2-hydroxy-, methyl ester; Benzene, 1-methoxy-4-(1E)-1-propen-1-yl-; 2,6-Octadiene, 1,1-dimethoxy-3,7-dimethyl-; Cyclohexanemethanol, α,3,3-trimethyl-, 1-formate; 2-Decenal, (2E)-; 3-Cyclopentene-1-acetonitrile, 2,2,3-trimethyl-; 2-Cyclohexen-1-one, 2-methyl-5-(1-methylethenyl)-, (5R)—; Cyclohexanone, 4-(1,1-dimethylpropyl)-; 2-Cyclohexen-1-one, 3-methyl-5-propyl-; Benzonitrile, 4-(1-methylethyl)-; 2,6-Nonadienenitrile; Butanoic acid, 2-methyl-, (3Z)-3-hexen-1-yl ester; Benzene, 1-(cyclopropylmethyl)-4-methoxy-; 2-Nonynoic acid, methyl ester; Acetic acid, 2-phenylethyl ester; Cyclohexanol, 2-(1,1-dimethylethyl)-; 2,6-Nonadien-1-ol; Propanoic acid, 2-methyl-, phenylmethyl ester; Bicyclo[2.2.1]heptan-2-ol, 1,2,3,3-tetramethyl-, (1R,2R,4S)-rel-; Benzaldehyde, 4-(1-methylethyl)-; 2,5-Octadien-4-one, 5,6,7-trimethyl-, (2E)-; 3-Cyclohexen-1-ol, 4-methyl-1-(1-methylethyl)-; 3-Cyclohexene-1-methanol, 2,4,6-trimethyl-; Pentanoic acid, (3Z)-3-hexen-1-yl ester; Bicyclo[2.2.1]heptan-2-ol, 1,7,7-trimethyl-, 2-propanoate, (1R,2R,4R)-rel-; Benzene, 1-methyl-4-(1-methylethyl)-2-(1-propen-1-yl)-; 2,4-Nonanedione, 3-methyl-; 3-Cyclohexene-1-propanal, β,4-dimethyl-; 1-Hexanol, 5-methyl-2-(1-methylethyl)-, (2R)—; 3-Heptanone, 5-methyl-, oxime; 2(3H)-Furanone, 5-butyldihydro-; 1-Nonanol; Acetic acid, 2-(3-methylbutoxy)-, 2-propen-1-yl ester; Bicyclo[2.2.1]heptan-2-ol, 1,7,7-trimethyl-, (1S,2R,4S)—; Bicyclo[2.2.1]heptan-2-ol, 1,7,7-trimethyl-, (1R,2R,4R)-rel-; Cyclohexanol, 2-(1,1-dimethylpropyl)-, 1-acetate; 3-Cyclohexene-1-methanol, α,α,4-trimethyl-, 1-acetate; Cyclohexanemethanol, α,α,4-trimethyl-; 10-Undecenal; 1-Octanol, 3,7-dimethyl-; Furan, tetrahydro-2,4-dimethyl-4-phenyl-; Benzene, [2-(3-methylbutoxy)ethyl]-; Butanoic acid, phenylmethyl ester; Benzoic acid, 2-hydroxy-, ethyl ester; Cyclohexanol, 4-(1,1-dimethylethyl)-; 1,6-Octadien-3-ol, 3,7-dimethyl-, 3-formate; Dodecanal; 3,6-Nonadien-1-ol, (3Z,6Z)—; Decanenitrile; Cyclohexanol, 5-methyl-2-(1-methylethyl)-, (1R,2S,5R)—; Propanoic acid, 2-methyl-, 4-methylphenyl ester; Propanoic acid, 2-methyl-, (1R,2S,4R)-1,7,7-trimethylbicyclo[2.2.1]hept-2-yl ester, rel-; Acetaldehyde, 2-(4-methylphenoxy)-; 2-Butenoic acid, 2-methyl-, (3Z)-3-hexen-1-yl ester, (2E)-; Bicyclo[3.1.1]hept-2-ene-2-propanal, 6,6-dimethyl-; 2-Nonanol, 6,8-dimethyl-; Cyclohexanol, 1-methyl-3-(2-methylpropyl)-; 1H-Indole; 2-Undecenal; 2H-Pyran-2-one, 4,6-dimethyl-; 3-Cyclohexene-1-methanol, α,α,4-trimethyl-; 3-Hepten-2-one, 3,4,5,6,6-pentamethyl-, (3Z)—; 2(3H)-Furanone, 5-butyldihydro-4-methyl-; 7-Octen-2-ol, 2,6-dimethyl-, 2-acetate; 2-Propenal, 3-phenyl-; 1,6-Octadien-3-ol, 3,7-dimethyl-, 3-propanoate; 1,6-Nonadien-3-ol, 3,7-dimethyl-, 3-acetate; Cyclopentanone, 2,2,5-trimethyl-5-pentyl-; 2,6-Octadien-1-ol, 3,7-dimethyl-, 1-acetate, (2Z)—; 2,6-Octadien-1-ol, 3,7-dimethyl-, 1-acetate, (2E)-; Undecane, 1,1-dimethoxy-2-methyl-; Benzenemethanol, α-methylene-, 1-acetate; Benzaldehyde, 4-methoxy-; Cyclohexanol, 5-methyl-2-(1-methylethenyl)-, 1-acetate, (1R,2S, 5R)—; 6-Octenenitrile, 3,7-dimethyl-; 6-Octen-2-ol, 2,6-dimethyl-; Benzene, 1,1'-oxybis-; Benzoic acid, butyl ester; 5,8-Methano-2H-1-benzopyran, 6-ethylideneoctahydro-; Cyclohexanepropanol, α,α-dimethyl-; Benzenepropanal, β-methyl-3-(1-methylethyl)-; Benzenemethanol, 4-methoxy-, 1-acetate; Phenol, 2-ethoxy-4-methyl-; Benzene, [2-(1-propoxyethoxy)ethyl]-; 7-Octen-1-ol, 3,7-dimethyl-; Bicyclo[4.3.1]decane, 3-methoxy-7,7-dimethyl-10-methylene-; Propanoic acid, 2-(1,1-dimethylpropoxy)-, propyl ester, (2S)—; Benzoic acid, 2-(methylamino)-, methyl ester; 6-Octen-1-ol, 3,7-dimethyl-, (3S)—; 7-Octen-2-ol, 2-methyl-6-methylene-; 4,6-Octadien-3-ol, 3,7-dimethyl-; 5-Oxatricyclo[8.2.0.04,6]dodecane, 4,9,12,12-tetramethyl-; 2-Cyclohexene-1-carboxylic acid, 2-ethyl-6,6-dimethyl-, ethyl ester; 3-Buten-2-one, 4-(2,6,6-trimethyl-1-cyclohexen-1-yl)-, (3E)-; 4,7-Methano-1H-inden-5-ol, octahydro-, 5-acetate; Benzoic acid, 2-amino-, methyl ester; Spiro[1,3-dioxolane-2,8'(5'H)-[2H-2,4a]methanonaphthalene], hexahydro-1',1',5',5'-tetramethyl-, (2'S,4'aS,8'aS)-(9CI); 3-Buten-2-one, 4-(2,6,6-trimethyl-2-cyclohexen-1- yl)-, (3E)-; Benzeneethanol, α,α-dimethyl-, 1-acetate; 4,7-Methano-1H-inden-5-ol, 3a,4,5,6,7,7a-hexahydro-, 5-acetate; 6-Octen-1-ol, 3,7-dimethyl-, 1-acetate; 2H-Pyran, tetrahydro-2-methyl-4-methylene-6-phenyl-; Bicyclo[3.3.1]nonane, 2-ethoxy-2,6,6-trimethyl-9-methylene-; 2,6-Octadien-1-ol, 3,7-dimethyl-, (2E)-; Bicyclo[7.2.0]undec-4-ene, 4,11,11-trimethyl-8-methylene-, (1R,4E,9S)—; 1H-3a,7-Methanoazulene, octahydro-6-methoxy-3,6,8,8-tetramethyl-, (3R,3aS,6S,7R,8aS)—; Bicyclo[7.2.0]undec-4-ene, 4,11,11-trimethyl-8-methylene-, (1R,4E,9S)—; 1H-Inden-1-one, 2,3-dihydro-2,3,3-trimethyl-; 2-Propanol, 1,1'-oxybis-; 2-Octanol, 7-methoxy-3,7-dimethyl-; 4,9-Decadienal, 4,8-dimethyl-; 3-Hexenoic acid, (3Z)-3-hexen-1-yl ester, (3Z)—; Bicyclo[2.2.1]hept-5-ene-2-carboxylic acid, 3-(1-methylethyl)-, ethyl ester, (1R,2S,3S,4S)-rel-; 2-Propen-1-ol, 3-phenyl-; Propanoic acid, 2-methyl-, 1-ethenyl-1,5-dimethyl-4-hexen-1-yl ester; Ethanol, 2-phenoxy-, 1-propanoate; 2-Propenoic acid, 3-phenyl-, methyl ester; Benzenepropanal, 2-ethyl-α,α-dimethyl-; Propanoic acid, decyl ester; Benzene, 1,2-dimethoxy-4-(1-propen-1-yl)-; 3-Decen-5-ol, 4-methyl-; Phenol, 2-methoxy-4-(2-propen-1-yl)-; 1-Propanone, 1-[2-methyl-5-(1-methylethyl)-2-cyclohexen-1-yl]-; 1,3-Benzodioxole-5-carboxaldehyde; 2-Dodecenal, (2E)-; Benzenepropanal, 4-methoxy-α-methyl-; 1,4-Cyclohexanedicarboxylic acid, 1,4-dimethyl ester; 2-Buten-1-one, 1-(2,6,6-trimethyl-3-cyclohexen-1-yl)-; 2-Butanone, 4-(2,6,6-trimethyl-1-cyclohexen-1-yl)-; 2-Propenenitrile, 3-phenyl-, (2E)-; Propanoic acid, 2-methyl-, 2-phenylethyl ester; 2-Cyclopenten-1-one, 3-methyl-2-(2Z)-2-penten-1-yl-; Acetaldehyde, 2-[(3,7-dimethyl-6-octen-1-yl)oxy]-; 1-Cyclohexene-1-ethanol, 4-(1-methylethyl)-, 1-formate; 2,4-Decadienoic acid, ethyl ester, (2E,4Z)—; 2-Propen-1-ol, 3-phenyl-, 1-acetate; Naphtho[2,1-b]furan, dodecahydro-3a,6,6,9a-tetramethyl-, (3aR,5aS,9aS,9bR)—; Benzenepropanal, 4-(1,1-dimethylethyl)-; 1,4-Methanonaphthalen-5(1H)-one, 4,4a,6,7,8,8a-hexahydro-; Dodecanoic acid, 12-hydroxy-, λ-lactone (6CI,7CI); 1,12-; Cyclohexanepropanoic acid, 2-propen-1-yl ester; 2(3H)-Furanone, 5-hexyldihydro-5-methyl-; 2,6-Nonadienenitrile, 3,7-dimethyl-; 10-Undecenoic acid, ethyl ester; Benzenepropanal, α-methyl-4-(1-methylethyl)-; 1-Oxaspiro[4.5]decan-2-one, 8-methyl-; 2(3H)-Furanone, dihydro-5-pentyl-; 2(3H)-Furanone, 5-hexyldihydro-; 2-Buten-1-one, 1-(2,6,6-trimethyl-2-cyclohexen-1-yl)-, (2E)-; 2-Buten-1-one, 1-(2,4,4-trimethyl-2-cyclohexen-1-yl)-, (2E)-; 2H-Pyran-2-one, tetrahydro-6-pentyl-; Benzenepropanal, 4-ethyl-α,α-dimethyl-; 1,3-Benzodioxole, 5-(diethoxymethyl)-; 4-Penten-1-one, 1-(5,5-dimethyl-1-cyclohexen-1-yl)-; Bicyclo[3.1.1]hept-2-ene-2-ethanol, 6,6-dimethyl-, 2-acetate; 2-Propenoic acid, 3-phenyl-, ethyl ester; 1,3-Dioxane, 2,4,6-trimethyl-4-phenyl-; Cyclododecane, (methoxymethoxy)-; Bicyclo[3.1.1]hept-2-ene-2-propanal, α,α,6,6-tetramethyl-; 2(3H)-Benzofuranone, hexahydro-3,6-dimethyl-; Benzeneacetonitrile, 4-(1,1-dimethylethyl)-; 2-Buten-1-one, 1-(2,6,6-trimethyl-1-cyclohexen-1-yl)-; 1,4-Methanonaphthalen-6(2H)-one, octahydro-7-methyl-; Bicyclo[3.2.1]octan-8-one, 1,5-dimethyl-, oxime; Benzenepentanol, γ-methyl-; Cyclohexene, 4-(1,5-dimethyl-4-hexen-1-ylidene)-1-methyl-; Phenol, 2-methoxy-4-propyl-; Benzoic acid, 2-hydroxy-, 2-methylpropyl ester; 2H-1-Benzopyran-2-one, octahydro-; Cyclohexanone, 2-(1-mercapto-1-methylethyl)-5-methyl-; 2-Oxiranecarboxylic acid, 3-methyl-3-phenyl-, ethyl ester; 3-Cyclohexene-1-carboxaldehyde, 4-(4-methyl-3-penten-1-yl)-; Propanoic acid, 2-methyl-, 2-phenoxyethyl ester; Indeno[1,2-d]-1,3-dioxin, 4,4a,5,9b-tetrahydro-; 2H-Pyran-4-ol, tetrahydro-4-methyl-2-(2-methylpropyl)-; Cyclohexanebutanal, α,2,6,6-tetramethyl-; 1,6-Nonadien-3-ol, 3,7-dimethyl-; 3-Buten-2-one, 4-(2,2,6-trimethyl-7-oxabicyclo[4.1.0]hept-1-yl)-; Phenol, 2-methoxy-4-(1-propen-1-yl)-; 2(3H)-Furanone, 5-hexyldihydro-4-methyl-; 1-Penten-3-one, 1-(2,6,6-trimethyl-2-cyclohexen-1-yl)-; 2-Buten-1-one, 1-(2,6,6-trimethyl-1,3-cyclohexadien-1-yl)-; 2-Cyclopenten-1-one, 2-hydroxy-3-methyl-; Propanoic acid, 2,2-dimethyl-, 2-phenylethyl ester; Dodecanenitrile; 6-Octen-1-ol, 3,7-dimethyl-, 1-propanoate; Benzenepentanal, (3-methyl-; Acetic acid, 2-phenoxy-, 2-propen-1-yl ester; Benzenepropanal, 4-(1,1-dimethylethyl)-α-methyl-; 4,7-Methano-1H-indene-2-carboxaldehyde, octahydro-5-methoxy-; Pentitol, 1,5-anhydro-2,4-dideoxy-2-pentyl-, 3-acetate; Cyclododecane, (ethoxymethoxy)-; 3-Buten-2-one, 4-(2,5,6,6-tetramethyl-2-cyclohexen-1-yl)-; Indeno[4,3a-b]furan, decahydro-2,2,7,7,8,9,9-heptamethyl-; Quinoline, 6-(1-methylpropyl)-; Carbonic acid, 4-cycloocten-1-yl methyl ester; 1H-Indene-5-propanal, 2,3-dihydro-3,3-dimethyl-; 3-Cyclohexene-1-carboxaldehyde, 1-methyl-3-(4-methyl-3-penten-1-yl)-; 6-Oxabicyclo[3.2.1]octane, 5-methyl-1-(2,2,3-trimethyl-3-cyclopenten-1-yl)-; 2H-Pyran-2-one, tetrahydro-6-(3-penten-1-yl)-; 2,4,7-Decatrienoic acid, ethyl ester; Butanoic acid, 3-methyl-, 2-phenylethyl ester; Spiro[1,4-methanonaphthalene-2(1H),2'-oxirane], 3,4,4a,5,8,8a-hexahydro-3',7-dimethyl-; Ethanol, 2-[[(1R,2R,4R)-1,7,7-trimethylbicyclo[2.2.1]hept-2-yl]oxy]-, rel-; Phenol, 2-methoxy-4-(1-propen-1-yl)-, 1-acetate; 2H-Indeno[4,5-b]furan, decahydro-2,2,6,6,7,8,8-heptamethyl-; Acetic acid, 2-(cyclohexyloxy)-, 2-propen-1-yl ester; Octanal, 7-hydroxy-3,7-dimethyl-; 1,6-Heptadien-3-one, 2-cyclohexyl-; 5-Thiazoleethanol, 4-methyl-; 1,4-Cyclohexanedicarboxylic acid, 1,4-diethyl ester; 2(3H)-Furanone, 5-heptyldihydro-; 1,3-Benzodioxole-5-propanal, α-methyl-; 4H-Inden-4-one, 1,2,3,5,6,7-hexahydro-1,1,2,3,3-pentamethyl-; Cyclohexanone, 4-(1-ethoxyethenyl)-3,3,5,5-tetramethyl-; Benzenepropanenitrile, α-ethenyl-α-methyl-; 9-Undecenal, 2,6,10-trimethyl-; Pyridine, 2-(3-phenylpropyl)-; Indeno[1,2-d]-1,3-dioxin, 4,4a,5,9b-tetrahydro-2,4-dimethyl-; Propanoic acid, 2-methyl-, 3a,4,5,6,7,7a-hexahydro-4,7-methano-1H-inden-5-yl ester; 1-Naphthalenol, 1,2,3,4,4a,7,8,8a-octahydro-2,4a,5,8a-tetramethyl-, 1-formate; Benzenepropanol, β,β,3-trimethyl-; 2-Cyclohexen-1-one, 4-(2-buten-1-ylidene)-3,5,5-trimethyl-; 3-Hexen-1-ol, 1-benzoate, (3Z)—; Benzaldehyde, 4-hydroxy-3-methoxy-; 1H-3a,7-Methanoazulen-6-ol, octahydro-3,6,8,8-tetramethyl-, 6-acetate, (3R,3aS,6R,7R,8aS)—; 4,7-Methano-1H-inden-6-ol, 3a,4,5,6,7,7a-hexahydro-8,8-dimethyl-, 6-propanoate; 2-Oxiranecarboxylic acid, 3-phenyl-, ethyl ester; 4H-4a,9-Methanoazuleno[5,6-d]-1,3-dioxole, octahydro-2,2,5,8,8,9a-hexamethyl-, (4 aR,5R,7aS,9R)—; 1H-Indene-2-methanol, 2,3-dihydro-2,5-dimethyl-; Butanoic acid, 1,1-dimethyl-2-phenylethyl ester; Cyclododeca[c]furan, 1,3,3a,4,5,6,7,8,9,10,11,13a-dodecahydro-; Benzenebutanenitrile, α,α,γ-trimethyl-; 2-Butanone, 4-(1,3-benzodioxol-5-yl)-; Benzoic acid, 4-hydroxy-3-methoxy-, methyl ester; 3-Cyclopentene-1-butanol, β,2,2,3-tetramethyl-2-Methyl-4-(2,2,3-trimethyl-3-cyclopenten-1-yl)butanol; 2-Butenal, 2-methyl-4-(2,6,6-trimethyl-1-cyclohexen-1-yl)-; 2-Naphthalenol, decahydro-2,5,5-trimethyl-; 1,7-Octanediol, 3,7-dimethyl-; 2H-1-Benzopyran-2-one; 1,3-Dioxolane, 2-[6-methyl-8-(1-methylethyl)bicyclo[2.2.2]oct-5-en-2-yl]-; Propanoic acid, 2,2-dimethyl-, 3a,4,5,6,7,7a-hexahydro-4,7-methano-1H-inden-6-yl ester; Butanoic acid, (2E)-3,7-dimethyl-2,6-octadien-1-yl ester; 2-Butanone, 4-(4-hydroxyphenyl)-; 10-Undecenoic acid, butyl ester; and combinations thereof.

In another embodiment, the fragrance composition comprises ethanol in the amount of from about 50% to about 80%, or from about 55% to about 75%, relative to the total weight of the composition.

In another embodiment, said perfume composition comprises one or more non-odorous fragrance co-modulators selected from the group consisting of:
   a) Isocetyl alcohol, for example CERAPHYL ICA;
   b) PPG-3 myristyl ether for example, Tegosoft APM and/or Varonic APM;
   c) Neopentyl glycol diethylhexanoate for example Schercemol NGDO; and
   d) mixtures thereof.
wherein the one or more non-odorous fragrance co-modulators are present in the amount of from about 0.05% to about 10%, preferably from about 0.5% to about 6%, relative to the total weight of the composition.

In one embodiment, said perfume composition comprises isocetyl alcohol.

In another embodiment, said perfume composition the non-odorous fragrance modulators are formed of at least 50% of PPG-20 Methyl Glucose Ether, relative to the combined weight of the non-odorous fragrance modulators and the non-odorous fragrance co-modulators.

In one embodiment, said perfume composition, said composition comprises:
   at least one low volatile fragrance material having a vapor pressure <0.001 Torr, in the amount of from about 0.1% to about 30%, relative to the total weight of the fragrance component;
   (i) at least one volatile fragrance material having a vapor pressure ≥0.001 Torr in the amount of from about 70% to about 99.9%, relative to the total weight of the fragrance component; and
   (ii) a non-odorous fragrance modulator formed of an alkoxylated methyl glucoside, preferably PPG-20 Methyl Glucose Ether, in the amount of from about 0.1% to about 20%, relative to the total weight of the composition.

Co-Modulators

In one aspect, of the fragrance composition the composition comprises one or more non-odorous fragrance co-modulators selected from the group consisting of Isocetyl alcohol, for example, CERAPHYL ICA; PPG-3 myristyl ether for example, Tegosoft APM and/or Varonic APM; Neopentyl glycol diethylhexanoate, for example, Schercemol NGDO; or mixtures thereof, in one aspect in the amount of from about 0.5% to about 6%, relative to the total weight of the composition.

Entrapment Materials

In yet another aspect, fragrance compositions of the present invention may comprise an entrapment material at a level such that the weight ratio of the entrapment material to the fragrance materials is in the range of from about 1:20 to about 20:1. Preferably, the fragrance composition may comprise an entrapment material present in the amount of from about 0.001% to about 40%, from about 0.1% to about 25%, from about 0.3% to about 20%, from about 0.5% to about 10%, or from about 0.75% to about 5%, relative to the total weight of the fragrance composition. The fragrance compositions disclosed herein may comprise from 0.001% to 40%, from 0.1% to 25%, from 0.3% to 20%, from 0.5% to 10% or from 0.75% to 5%, relative to the total weight of the composition, of a cyclic oligosaccharide.

Suitable entrapment materials for use herein are selected from polymers; capsules, microcapsules and nanocapsules; liposomes, absorbents; cyclic oligosaccharides and mixtures thereof. Preferred are absorbents and cyclic oligosaccharides and mixtures thereof. Highly preferred are cyclic oligosaccharides (see PCT Publication Nos. WO2000/67721 (Procter & Gamble); and WO2000/67720 (Procter & Gamble); and U.S. Pat. No. 6,893,647 (Procter & Gamble)).

As used herein, the term "cyclic oligosaccharide" means a cyclic structure comprising six or more saccharide units. Preferred for use herein are cyclic oligosaccharides having six, seven or eight saccharide units and mixtures thereof, more preferably six or seven saccharide units and even more preferably seven saccharide units. It is common in the art to abbreviate six, seven and eight membered cyclic oligosaccharides to $\alpha$, $\beta$ and $\gamma$ respectively.

The cyclic oligosaccharide of the compositions used for the present invention may comprise any suitable saccharide or mixtures of saccharides. Examples of suitable saccharides include, but are not limited to, glucose, fructose, mannose, galactose, maltose and mixtures thereof. However, preferred for use herein are cyclic oligosaccharides of glucose. The preferred cyclic oligosaccharides for use herein are $\alpha$-cyclodextrins or $\beta$-cyclodextrins, or mixtures thereof, and the most preferred cyclic oligosaccharides for use herein are $\beta$-cyclodextrins.

The cyclic oligosaccharide, or mixture of cyclic oligosaccharides, for use herein may be substituted by any suitable substituent or mixture of substituents. Herein the use of the term "mixture of substituents" means that two or more different suitable substituents can be substituted onto one cyclic oligosaccharide. The derivatives of cyclodextrins consist mainly of molecules wherein some of the OH groups have been substituted. Suitable substituents include, but are not limited to, alkyl groups; hydroxyalkyl groups; dihydroxyalkyl groups; (hydroxyalkyl)alkylenyl bridging groups such as cyclodextrin glycerol ethers; aryl groups; maltosyl groups; allyl groups; benzyl groups; alkanoyl groups; cationic cyclodextrins such as those containing 2-hydroxy-3-(dimethylamino) propyl ether; quaternary ammonium groups; anionic cyclodextrins such as carboxyalkyl groups, sulphobutylether groups, sulphate groups, and succinylates; amphoteric cyclodextrins; and mixtures thereof.

The substituents may be saturated or unsaturated, straight or branched chain. Preferred substituents include saturated and straight chain alkyl groups, hydroxyalkyl groups and mixtures thereof. Preferred alkyl and hydroxyalkyl substituents are selected from $C_1$-$C_8$ alkyl or hydroxyalkyl groups or mixtures thereof, more preferred alkyl and hydroxyalkyl substituents are selected from $C_1$-$C_6$ alkyl or hydroxyalkyl groups or mixtures thereof, even more preferred alkyl and hydroxyalkyl substituents are selected from $C_1$-$C_4$ alkyl or hydroxyalkyl groups and mixtures thereof. Especially preferred alkyl and hydroxyalkyl substituents are propyl, ethyl and methyl, more especially hydroxypropyl and methyl and even more preferably methyl.

Preferred cyclic oligosaccharides for use in the present invention are unsubstituted, or are substituted by only saturated straight chain alkyl, or hydroxyalkyl substituents. Therefore, preferred examples of cyclic oligosaccharides for use herein are $\alpha$-cyclodextrin, $\beta$-cyclodextrin, methyl-$\alpha$-cyclodextrin, methyl-$\beta$-cyclodextrin, hydroxypropyl-$\alpha$-cyclodextrin and hydroxypropyl-$\beta$-cyclodextrin. Most preferred examples of cyclic oligosaccharides for use herein are methyl-$\alpha$-cyclodextrin and methyl-$\beta$-cyclodextrin. These are available from Wacker-Chemie GmbH Hanns-Seidel-Platz 4, Munchen, DE under the tradename Alpha W6 M and Beta W7 M respectively. Especially preferred is methyl-$\beta$-cyclodextrin.

The cyclic oligosaccharides of the compositions used for the present invention are preferably soluble in water, ethanol, or both water and ethanol. As used herein "soluble" means at least about 0.1 g of solute dissolves in 100 mL of solvent, at 25° C. and 1 atm of pressure. Preferably the cyclic oligosaccharides for use herein have a solubility of at least about 1 g/100 mL, at 25° C. and 1 atm of pressure. Preferred is that cyclic oligosaccharides are only present at levels up to their solubility limits in a given composition at room temperature. A person skilled in the art will recognise that the levels of cyclic oligosaccharides used in the present invention will also be dependent on the components of the composition and their levels, for example the solvents used or the exact fragrance oils, or combination of fragrance oils, present in the composition. Therefore, although the limits stated for the entrapment material are preferred, they are not exhaustive.

Volatile Solvents

In yet another aspect, the present invention provides fragrance compositions, preferably fine fragrance compositions, which commonly contain high levels of ethanol or other alcohols (e.g., methanol, propanol, isopropanol, butanol, and mixtures thereof) commonly found in commercial fine fragrance products. Accordingly, ethanol may be present in any of the fragrance compositions of the present invention, and more specifically, it will form from about 10% to about 80%, or even from about 25% to about 75% of the composition, or combinations thereof, relative to the total weight of the composition. Alternatively, ethanol may be present in an amount of from about 10% or 25% to about 75% or 80%, relative to the total weight of the fragrance composition. Any acceptable quality of ethanol, compatible and safe for the specific intended use of the fragrance composition such as, for example, topical applications of fine fragrance, and is convenient for use in the fragrance compositions according to the present invention.

Non-Volatile Solvents

The fragrance composition may comprise a non-volatile solvent or a mixture of non-volatile solvents. Non-limiting examples of non-volatile solvents include benzyl benzoate, diethyl phthalate, isopropyl myristate, propylene glycol, dipropylene glycol, methyl citrate, and mixtures thereof. If present, the non-volatile solvent may be included at a weight ratio of the non-volatile solvent to the cyclic oligosaccharide of less than 1:1, less than 1:2, less than 1:10, or less than 1:100. The non-volatile solvent may also be included at a weight ratio of the non-volatile solvent to the cyclic oligosaccharide of less than about 1:1, less than about 1:2, less than about 1:10, or less than about 1:100.

Water

In yet another aspect, water may be present in any of the fragrance compositions of the present invention, and more specifically, it shall not exceed about 40%, preferably about 20% or less, or more preferably about 10% or less, relative to the total weight of the composition. Alternatively, water may be present in an amount of from about 10% or 20% to about 40%, relative to the total weight of the fragrance composition. It is understood that the amount of water present in the fragrance composition may be from the water present in the ethanol used in the fragrance composition, as the case may be.

Propellants

The fragrance compositions described herein may include a propellant. Some examples of propellants include compressed air, nitrogen, inert gases, carbon dioxide, and mixtures thereof. Propellants may also include gaseous hydrocarbons like propane, n-butane, isobutene, cyclopropane, and mixtures thereof. Halogenated hydrocarbons like 1,1-difluoroethane may also be used as propellants. Some non-limiting examples of propellants include 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), and 152A (1,1 diflouroethane). The propellant may have a concentration from about 15%, 25%, 30%, 32%, 34%, 35%, 36%, 38%, 40%, or 42% to about 70%, 65%, 60%, 54%, 52%, 50%, 48%, 46%, 44%, or 42% by weight of the total fill of materials stored within the container.

Other Ingredients

In yet another aspect, the fragrance composition consists essentially of the recited ingredients but may contain small amounts (not more than about 10%, preferably no more than 5%, or preferably no more than 2% thereof, relative to the total weight of the fragrance composition) of other ingredients that do not impact on the fragrance profile, particularly the evaporation rate, habituation effect, and release of the fragrance materials. For example, the fragrance composition may comprise stabilizing or anti-oxidant agents, UV filters or quenchers, or colouring agents, commonly used in perfumery. There are a number of other examples of additional ingredients that are suitable for inclusion in the present fragrance compositions. These include, but are not limited to, alcohol denaturants such as denatonium benzoate; UV stabilisers such as benzophenone-2; antioxidants such as tocopheryl acetate; preservatives such as phenoxyethanol, benzyl alcohol, methyl paraben, and propyl paraben; dyes; pH adjusting agents such as lactic acid, citric acid, sodium citrate, succinic acid, phosphoric acid, sodium hydroxide, and sodium carbonate; deodorants and anti-microbials such as farnesol and zinc phenolsulphonate; humectants such as glycerine; oils; skin conditioning agents such as allantoin; cooling agents such as trimethyl isopropyl butanamide and menthol; hair conditioning ingredients such as panthenol, panthetine, pantotheine, panthenyl ethyl ether, and combinations thereof; silicones; solvents such as hexylene glycol; hair-hold polymers such as those described in PCT Publication WO94/08557 (Procter & Gamble); salts in general, such as potassium acetate and sodium chloride and mixtures thereof.

In yet another aspect, the fragrance composition of the present invention, depending on its intended use, is a mixture of fragrance materials possibly together with other ingredients such as, for example, perfume carriers. By the term "perfume carrier", it is meant to include materials which are practically neutral from a perfumery point of view, i.e., which does not significantly alter the organoleptic properties of perfuming components. The perfume carrier may be a compatible liquid or solid fillers, diluents, extenders and the like. The term "compatible", as used herein, means that the components of the fragrance compositions of this invention are capable of being combined with the primary actives of the present invention, and with each other, in a manner such that there is no interaction which would substantially reduce the efficacy of the fragrance composition under ordinary use situations. The type of carrier utilized in the present invention depends on the type of product desired and may comprise, but are not limited to, solutions, aerosols, emulsions (including oil-in-water or water-in-oil), gels, and liposomes. Preferably, the carrier is a liquid and will be a solvent such as, for example, dipropyleneglycol, diethyl phthalate, isopropyl myristate, benzyl benzoate, 2-(2-ethoxyethoxy)-1-ethanol, or ethyl citrate (triethyl citrate).

Article of Manufacture

The fragrance composition may be included in an article of manufacture comprising a spray dispenser. The spray dispenser may comprise a vessel for containing the composition to be dispensed. The spray dispenser may comprise an aerosolized composition (i.e. a composition comprising a propellant) within the vessel as well. Other non-limiting examples of spray dispensers include non-aerosol dispensers (e.g. vapor sprays), manually activated dispensers, pump-spray dispensers, or any other suitable spray dispenser available in the art.

Methods of Using the Fragrance Compositions

The fragrance composition of the present invention according to any embodiments described herein is a useful perfuming composition, which can be advantageously used as consumer products intended to perfume any suitable substrate. As used herein, the term "substrate" means any surface to which the fragrance composition of the present invention may be applied to without causing any undue adverse effect. For example, this can include a wide range of surfaces including human or animal skin or hair. Preferred substrates include body surfaces such as, for example, hair and skin, most preferably skin.

The fragrance composition of the present invention may be used in a conventional manner for fragrancing a substrate. An effective amount of the fragrance composition, typically from about 1 μL to about 10,000 μL, preferably from about 10 μL to about 1,000 μL, more preferably from about 25 μL to about 500 μL, or most preferably from about 50 μL to about 100 μL, or combinations thereof, is applied to the suitable substrate. Alternatively, an effective amount of the fragrance composition of the present invention is from about 1 μL, 10 μL, 25 μL or 50 μL to about 100 μL, 500 μL, 1,000 μL or 10,000 μL. The fragrance composition may be applied by hand or applied utilizing a delivery apparatus such as, for example, vaporizer or atomizer. Preferably, the fragrance composition is allowed to dry after its application to the substrate. The scope of the present invention should be considered to cover one or more distinct applications of the fragrance composition or the continuous release of a fragrance composition via a vaporizer or other type of atomizer.

In one embodiment, present invention preferably relates to fragrance compositions in the form of a perfume, an eau de toilette, an eau de parfum, a cologne, a body splash, or a body spray. Therefore, according to this embodiment, the present invention provides a method of modifying or enhancing the odour properties of a body surface, preferably hair or skin, comprising contacting or treating the body surface with a composition of the present invention.

In another embodiment, the present invention relates to a method of resisting the fragrance habituation of a fragrance composition by a consumer, the method comprising administering a fragrance composition as described herein above to the consumer.

In yet another embodiment, the present invention relates to a method of producing a fragrance product comprising bringing into contact or mixing into the product an organoleptically active quantity of a fragrance composition as described herein above.

Test Methods

The following assays set forth must be used in order that the invention described and claimed herein may be more fully understood.

Test Method 1: Determining Vapor Pressure

In order to determine the vapor pressure for the fragrance materials, go to the website haps://scifinder.cas.org/scifinder/view/scifinder/scifinderExplorejsf and follow these steps to acquire the vapor pressure.

1. Input the CAS registry number for the particular fragrance material.
2. Select the vapor pressure from the search results.
3. Record the vapor pressure (given in Torr at 25° C.).

SciFinder uses Advanced Chemistry Development (ACD/Labs) Software Version 11.02. (© 1994-2013). If the CAS number for the particular fragrance material is unknown or does not exist, you can utilize the ACD/Labs reference program to directly determine the vapor pressure.

Test Method 2: Degree of Habituation

The Degree of Habituation to a fragrance composition containing a perfume raw material can be determined by exposing a human panel to daily exposures of the perfume over a four week period. The Degree of Habituation can be calculated at both the week two and week four time points, relative to the initial baseline time point.

For each exposure panel test, more than 15 panelists are recruited, and then exposed to the test scent in a manner, frequency, and concentration indicated by the intended product end use, but including at least one exposure per day every day for four consecutive weeks. The perfume exposure must be sufficient that the panelists can detect the perfume of interest being delivered from the product or perfume delivery system contained within the product. The criteria for recruitment onto the exposure panel requires that panelists be typical consumers of the product in question, who agree to use the scent being tested, are non-smokers, and free of nasal congestion and allergies. The degree of habituation is calculated and reported as the percent change in the Odor Detection Threshold (ODT) value at week 2 and at week 4, versus the initial baseline ODT value. Since the degree of habituation is a relative measure, it accommodates the variation in absolute ODT values which can arise between different testing laboratories.

Raw materials and finished products comprising them can be used in conjunction in order to determine the degree of habituation. For example, daily exposures to the panelists may involve the use of a finished product while the ODT test measurements may involve the use of the respective neat perfume or PRMs. The conditions selected for use in either the daily exposures or in the ODT testing must be applied uniformly across all panelists, and remain unchanged for the entirety of the testing period. When the test perfume materials are available in their simple forms i.e., PRMs, neat perfumes, or fine fragrances, unincorporated into complex products or delivery systems, then the ODT test is to be conducted with these simple forms via an olfactometer, as this is the preferred method.

When these simple forms of the test perfume materials are inaccessible for testing, then the ODT test may be conducted with finished products or complex formulations comprising the test perfume materials. Presentation devices other than an olfactometer may be required when conducting the ODT testing on finished products or complex formulations, and may include devices such as sniff cups, headspace chambers and capped bottles, as allowed for in the test method ASTM E679-04 described below.

The ODT value for each panelist is determined at each of three time points the during four week daily exposure period, namely; at an initial baseline, at two weeks, and at four weeks. The ODT values are always determined in accordance with test method ASTM E679-04 (Standard Practice for Determination of Odor and Taste Thresholds by a Forced-Choice Ascending Concentration Series of Limits) as reapproved in 2011 except, the following replaces the protocol of such test method's Sub-articles 4.4, 8.2 and 8.3.

Sub-article 4.4, Individual best-estimate values of the threshold are derived from the pattern of correct/incorrect responses produced separately by each panelist. The group average ODT value at a given time point is derived by fitting the entire data set from all panelists at that time point to a Log Logistic Regression Model.

Sub-article 8.2, If the concentration range has been correctly selected, it is not necessary that all panelists judge correctly within the range of concentration steps provided. Thus, the representation of the panelists' judgments as in 8.1 need not terminate with two or more consecutive plusses (+).

Sub-article 8.3, Since there is a finite probability that a correct answer will occur by chance alone, it is important that a panelist repeat the test three times. Panelists who fail the test at the highest concentration, are deemed anomic to the test material and their response is removed from the data set.

Additionally, the following selections are made in accordance with the test method's sub-articles 1.3, 1.4, 1.6, 1.7, and 4.1, and specified here as per sub-article 9.3.

Sub-article 1.3, The threshold is characterized as being a) only detection (awareness) that a very small amount of added substance is present but not necessarily recognizable.

Sub-article 1.4, When the preferred method is being conducted, namely using a simple perfume form presented via olfactometer, then the presentation medium is an air and pure nitrogen mix. When testing finished or complex products, alternative presentation media may be used, such as air.

Sub-article 1.6, When the preferred method is being conducted, namely using a simple perfume form presented via olfactometer, then the physical method of presentation is at a rate of 40 L/min. When testing finished or complex products, alternative presentation devices may be used, including but not limited to sniff cups, headspace chambers or capped bottles.

Sub-article 1.7, Presentation is made to a panel of greater than 15 panelists, who are participating in the daily exposure panel.

Sub-article 4.1, Eight scale steps are used, with each step having an individual predetermined dilution factor suitable for the stimuli being tested, at a temperature of 35° C. PRM or neat perfume stimuli are typically introduced to the olfactometer system in the neat form via a pump syringe. Sometimes a dilution of the stimuli with ethanol is needed.

The group average ODT values from the three time points are used to calculate the degree of habituation. The degree of habituation is reported for 2 specific time points, as the percent change in group average ODT at one time point, relative to the group average ODT at the initial baseline time point. The degree of habituation is determined at the time points of: 2 weeks and 4 weeks, of the four week daily exposure period, using the following formula:

Degree of Habituation(percent change in ODT) at Time $X$=((Group Average $ODT_{(Time\ X)}$−Group Average $ODT_{(Baseline)}$)/Group Average $ODT_{(Baseline)}$)×100 where Time X is either 2 weeks, or 4 weeks, of repeated daily exposure.

Anti-habituation Index:

A perfume is considered to have an anti-habituation index of:

For a two week test:
  Zero (0) when the Degree of Habituation after 2 weeks of exposure to said perfume is from about 150% to 25%.
  One (1) when the Degree of Habituation after 2 weeks of exposure to said perfume is less than 25% but greater than 10%.
  Two (2) when the Degree of Habituation after 2 weeks of exposure to said perfume is from 10% to 0%.
  Three (3) when the Degree of Habituation after 2 weeks of exposure to said perfume is less than 0% to about −25%.
  Four (4) when the Degree of Habituation after 2 weeks of exposure to said perfume is less than −25% to about −500%.

For a four week test:
  Zero (0) when the Degree of Habituation after 4 weeks of exposure to said perfume is from about 150% to 25%.
  One (1) when the Degree of Habituation after 4 weeks of exposure to said perfume is less than 25% but greater than 10%.
  Two (2) when the Degree of Habituation after 4 weeks of exposure to said perfume is from 10% to 0%.
  Three (3) when the Degree of Habituation after 4 weeks of exposure to said perfume is less than 0% to about −25%.
  Four (4) when the Degree of Habituation after 4 weeks of exposure to said perfume is less than −25% to about −500%.

EXAMPLES

The following examples are provided to further illustrate the present invention and are not to be construed as limitations of the present invention, as many variations of the present invention are possible without departing from its spirit or scope.

Example 1

Composition Comprising Anti-habituation Perfumes

Certain perfume raw materials can be incorporated into a fragrance compositions to resist the habituating effect inherent to the base perfume. Examples of some formulated habituation-resistant perfume raw materials suitable for incorporation into fragrance compositions are disclosed in Table 1. The perfume raw materials in Table 1 include pyrazine, oxime, sulfide, and thiazole-based moieties, respectively. Additionally, a nitrogen-based habituation reducing oxime group is included in the labienoxime compound.

TABLE 1

Perfumes with Anti-Habituation

| Ingredients | PRM Vapour Pressure (Torr) | A (wt %) | B (wt %) | C (wt %) | D (wt %) | E (wt %) | F (wt %) | G (wt %) | H (wt %) |
|---|---|---|---|---|---|---|---|---|---|
| Babylon oil § (94-2012C) | — | 100 | 99.20 | — | 99.00 | 99.60 | 99.60 | 99.80 | — |
| Babylon oil nil PRMs ‡ (Mod94nil ARCH MOD1) | — | — | — | 100 | — | — | — | — | — |
| Fresh Floral Fragrance (see Table 1a) | — | — | — | — | — | — | — | — | 99.20 |
| Dimethyl Sulphide* (0.1% in Dipropylene glycol) (CAS#75-18-3) | 647 | — | 0.10 | — | — | — | — | — | 0.10 |
| Dibutyl Sulphide* (0.1% in Dipropylene glycol) (CAS#544-40-1) | 0.816 | — | 0.10 | — | 1.00 | — | — | — | 0.10 |
| 2,4,4,7-Tetramethyl-6,8-nonadiene-3-one oxime † (10% in isoprorpyl myrisate and triethyl citrate IPM-TEC further diluted at 10% in Dipropylene glycol) (CAS#81783-01-9) | 0.000173 | — | — | — | — | — | — | 0.20% | — |
| 2,4,4,7-Tetramethyl-6,8-nonadiene-3-one oxime † (10% in isoprorpyl myrisate and triethyl citrate IPM-TEC further diluted at 1% in Dipropylene glycol)) (CAS#81783-01-9) | 0.000173 | — | 0.40 | — | — | — | — | — | 0.40 |
| 4-Methyl-5-thiazoleethanol †† (10% in Dipropylene glycol) (CAS#137-00-8) | 0.00297 | — | 0.10 | — | — | — | 0.40 | — | 0.10 |
| 2-Methylthio-3(5/6)-Methyl Pyrazine* (0.01% in Dipropylene Glycol) (CAS#67952-65-2) | 0.141-0.150 | — | 0.10 | — | — | 0.40 | — | — | 0.10 |
| TOTAL: | | 100% | 100% | 100% | 100% | 100% | 100% | 100% | 100% |

*Dimethyl sulphide, Dibutyl sulphide and 2-Methylthio-3(5/6)-Methyl Pyrazine is available from R.C. Treatt & Co. Ltd Bury St Edmunds, Suffolk, IP32 6NL, United Kingdom.
† 2,4,4,7-Tetramethyl-6,8-nonadiene-3-one oxime is supplied as Labienoxime 10 by Givaudan SA, 55 Voie des Bans, F-95102 ARGENTEUIL, France as a 10% active in isopropyl myristate and triethyl citrate. In order to enable addition to the oil the material was further diluted in Dipropylene Glycol at either 10% or 1%.
†† 4-Methyl-5-thiazoleethanol is supplied as Sulfurol by R.C. Treatt & Co. Ltd Bury St Edmunds, Suffolk, IP32 6NL, United Kingdom.
§ Babylon oil contains some very low levels of the perfume raw materials that may have resistance to habituation and is internal to The Procter & Gamble Co.
‡ Babylon oil nil PRMs does not contain any perfume raw materials having resistance to habituation effect and is internal to The Procter & Gamble Co.

TABLE 1a

Fresh Floral Fragrance

| Ingredients | CAS Number | Vapor Pressure (Torr) | Parts (wt %) |
|---|---|---|---|
| Benzyl acetate | 140-11-4 | 0.1640 | 11.0 |
| Linalool | 78-70-6 | 0.0905 | 10.0 |
| Phenethyl alcohol | 60-12-8 | 0.0741 | 16.0 |
| Indole | 120-72-9 | 0.0298 | 3.0 |
| α-Terpineol | 98-55-5 | 0.0283 | 3.0 |
| Geranyl acetate | 105-87-3 | 0.0256 | 4.0 |
| Cymal | 103-95-7 | 0.00881 | 6.0 |
| Hydroxycitronellal | 107-75-5 | 0.00318 | 23.0 |
| Majantol | 103694-68-4 | 0.00224 | 16.0 |
| Hexyl cinnamic aldehyde | 101-86-0 | 0.000697 | 8.0 |

Example 2

Production Formulations

Exemplary formulations of the fragrance compositions containing the above listed PRMs having anti-habituation effect.

TABLE 2

Fine Fragrance Compositions

| Ingredients | Compositions (wt %)[1] | | | | | | | |
|---|---|---|---|---|---|---|---|---|
| | Ex. 1 | Ex. 2 | Ex. 3 | Ex. 4 | Ex. 5 | Ex. 6 | Ex. 7 | Ex. 8 |
| Perfume A | 14% | — | — | — | — | — | — | — |
| Perfume B | — | 14% | — | — | — | — | — | 14% |
| Perfume C | — | — | 14% | — | — | — | — | — |
| Perfume D | — | — | — | 14% | — | — | — | — |
| Perfume E | — | — | — | — | 14% | — | — | — |
| Perfume F | — | — | — | — | — | 14% | — | — |
| Perfume G | — | — | — | — | — | — | 14% | — |
| Cavasol W7 methylated Beta-cyclodextrin (CAS # 128446-36-6) | — | — | — | — | — | — | — | 5% |
| Ethanol (96%) CAS#99678928 | | | | | 75% | | | |
| Uvinul CAS#95181238 | 0.3% | 0.3% | 0.3% | 0.3% | 0.3% | 0.3% | 0.3% | 0.3% |
| DI Water CAS#10000001 | q.s. | q.s. | q.s. | q.s. | q.s. | q.s. | q.s. | q.s. |
| TOTAL: | 100% | 100% | 100% | 100% | 100% | 100% | 100% | 100% |

[1]Wt % is relative to the total weight of the composition.

TABLE 3

Fine Fragrance Compositions with modulators and co-modulators

| Ingredients | Compositions (wt %)[1] | |
|---|---|---|
| | Ex. 9 | Ex. 10 |
| Perfume H | 7% | 7% |
| Glacam™ P-20 | 15% | 7.5% |
| Isocetyl alcohol CERAPHYLICA | — | 7.5% |
| Ethanol (96%) CAS#99678928 | 75% | 75% |
| Uvinul CAS#95181238 | 0.3% | 0.3% |
| DI Water CAS#10000001 | q.s. | q.s. |
| TOTAL: | 100% | 100% |

[1]Wt % is relative to the total weight of the composition.

TABLE 4

Body Spray Compositions

| Ingredients | CAS Number | Compositions (wt %) | |
|---|---|---|---|
| Denatured Ethanol | 64-17-5 | 39.70 | 59.45 |
| Water | 7732-18-5 | — | 0.75 |
| Dipropylene Glycol | 25265-71-8 | 15.00 | — |
| Isopropyl Myristate | 110-27-0 | 1.00 | — |
| Zinc Phenosulphonate | 127-82-2 | 0.50 | — |
| Cavasol W7 methylated Beta-cyclodextrin | 128446-36-6 | — | 1.00 |
| Fragrance[1] | — | 1.20 | 1.20 |
| Propane | 74-98-6 | 4.86 | — |
| Isobutane | 72-28-5 | 27.14 | — |
| 1,1-Difluoroethane (HFC-152a) | 75-37-6 | 8.00 | 35.00 |

[1]Can be any of fragrances B, D, E, F or G.

All documents cited in the Detailed Description are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern. The perfume raw materials disclosed, claimed and/or used in the perfumes claimed and/or described herein encompass any stereoisomers of such perfume raw materials.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fragrance composition comprising a fragrance oil such that the fragrance oil resists the fragrance habituation of a consumer to the fragrance composition, and wherein the fragrance oil comprises one or more perfume raw materials comprising from about 0.000001% to about 0.002% of 1-butylsulfanylbutane, based on the total perfume weight.

2. The fragrance composition according to claim 1, comprising from 0.001% to 30%, by weight of the fragrance composition, of the fragrance oil.

3. The fragrance composition according to claim 2, comprising from 5% to 15%, by weight of the fragrance composition, of the fragrance oil.

4. The fragrance composition according to claim 1, wherein the composition exhibits an anti-habituating effect on a consumer.

5. The fragrance composition according to claim 4 having:
   a) a two week anti-habituation index of 0, 1, 2, 3 or 4; and/or
   b) a four week anti-habituation index of 0, 1, 2, 3 or 4.

6. The fragrance composition according to claim 1, wherein the 1-butylsulfanylbutane is below its odor detection threshold.

7. A method of producing a fine fragrance product comprising bringing into contact or mixing into the product an organoleptically active quantity of a fragrance composition according to claim 1.

* * * * *